United States Patent
Mizomoto et al.

(10) Patent No.: US 8,602,221 B2
(45) Date of Patent: Dec. 10, 2013

(54) SEPARATION MEMBRANE FOR USE IN TREATMENT OF LIQUID COMPRISING AROMATIC ETHER POLYMER HYDROPHILIZED WITH HYDROPHILIZING AGENT

(75) Inventors: Hitoshi Mizomoto, Tokyo (JP); Junichi Shishido, Tokyo (JP); Shinya Hamasaki, Tokyo (JP); Hirofumi Miura, Tokyo (JP)

(73) Assignee: Asahi Kasei Kabuhiki Kaisha, Osaka-Shi (JP)

(*) Notice: Subject to any disclaimer, the term of this patent is extended or adjusted under 35 U.S.C. 154(b) by 1105 days.

(21) Appl. No.: 11/990,082

(22) PCT Filed: Aug. 4, 2006

(86) PCT No.: PCT/JP2006/315902
§ 371 (c)(1),
(2), (4) Date: Apr. 3, 2008

(87) PCT Pub. No.: WO2007/018284
PCT Pub. Date: Feb. 15, 2007

(65) Prior Publication Data
US 2009/0127186 A1    May 21, 2009

(30) Foreign Application Priority Data

Aug. 9, 2005  (JP) .................. 2005-230518
Feb. 13, 2006 (JP) .................. 2006-035489
Feb. 21, 2006 (JP) .................. 2006-043278

(51) Int. Cl.
B01D 71/52    (2006.01)

(52) U.S. Cl.
USPC ............ 210/500.33; 210/500.23; 210/500.28; 210/653

(58) Field of Classification Search
USPC .................. 210/500.33, 500.23, 500.28, 653
See application file for complete search history.

(56) References Cited

U.S. PATENT DOCUMENTS 4,698,388 A * 10/1987 Ohmura et al. ................ 525/88
4,776,959 A   10/1988 Kasai et al.
(Continued)

FOREIGN PATENT DOCUMENTS

EP    0856352 A1    8/1998
JP    61-161103 A   7/1986
(Continued)

OTHER PUBLICATIONS

Berghmans et al., "Phase behaviour and structure formation in solutions of poly(2,6-dimethyl-1,4-phenylene ether)," Polymer, vol. 36, No. 16, 1995, pp. 3085-3091.

(Continued)

*Primary Examiner* — David C Mellon
(74) *Attorney, Agent, or Firm* — Birch, Stewart, Kolasch & Birch, LLP

(57) ABSTRACT

[Problems] To provide a novel hydrophilized separation membrane for use in the treatment of a liquid, which comprises an aromatic ether polymer, is less likely to be degraded by sterilization with a high energy ray and has a controlled pore size and a high water permeability.

[Means for Solving Problems] A porous separation membrane for use in the treatment of a liquid which is produced by a wet film formation process using an aromatic ether polymer and a hydrophilizing agent. The separation membrane can be used for medical purposes or in a pharmaceutical of food.

2 Claims, 5 Drawing Sheets

(56) References Cited

U.S. PATENT DOCUMENTS

| | | | |
|---|---|---|---|
| 4,948,508 A | | 8/1990 | Nakagawa et al. |
| 5,057,218 A | | 10/1991 | Koshoji et al. |
| 5,700,903 A | * | 12/1997 | Hancock et al. ............. 528/373 |
| 6,495,043 B1 | | 12/2002 | Heijnen |

FOREIGN PATENT DOCUMENTS

| | | | |
|---|---|---|---|
| JP | 3-254826 A | | 11/1991 |
| JP | 4-4028 A | | 1/1992 |
| JP | 06-228887 A | | 8/1994 |
| JP | 2004-236788 A | | 8/2004 |
| JP | 2005-193201 A | | 7/2005 |
| WO | WO 97/13575 A1 | | 4/1997 |
| WO | WO 03/049775 A2 | * | 6/2003 |

OTHER PUBLICATIONS

Japanese Office Action mailed Jul. 11, 2012 for Japanese Application No. 2007-529635.

* cited by examiner

SEPARATION MEMBRANE FOR USE IN TREATMENT OF LIQUID COMPRISING AROMATIC ETHER POLYMER HYDROPHILIZED WITH HYDROPHILIZING AGENT

TECHNICAL FIELD

The present invention relates to a novel separation membrane for treating liquid made from an aromatic ether polymer hydrophilized by a hydrophilizing agent and exhibiting minimal deterioration by sterilization.

BACKGROUND ART

An aromatic ether polymer has been widely studied as a gas separation membrane due to the high physical strength, high solvent resistance, and high water resistance which is expressed based on its high hydrophobic property and particularly due to the very excellent gas permeability in the past.

For example, in the case of assuming a gas separation membrane for separating nitrogen gas and oxygen gas, since it is difficult to separate nitrogen gas from the gas composition mixed with oxygen gas by the difference in their molecular sizes, it is usually necessary to cause the membrane to express its separating performance by the difference in solubility and diffusibility of each gas component in the membrane. Therefore, in order to increase the gas separation and permeation performance, major effort has been directed to densifying the pore size on the membrane surface to 1.0 nm or less (refer to Non-patent Document 1), providing a dense layer as thin as possible on the membrane surface (refer to Patent Document 1), and increasing the gas solubility rate into the membrane material by suitable chemical modification, for example, by introducing an appropriate charge structure onto the membrane surface.

From the viewpoint of the membrane manufacturing process and the membrane structure, a hollow fiber membrane produced by a melt casting/spinning method utilizing thermally-induced phase separation has been reported (refer to Non-patent Document 2). The resulting hollow fiber membrane has a uniform porous structure from the inner surface to near the outer surface of the hollow fiber, and only the outermost surface has a completely blocked non-porous structure. The membrane is useful as a membrane aimed for gas separation.

A dense membrane of an aromatic ether polymer having a surface chemically modified by providing a charge structure, for example, has been used for a number of other applications, in which it is difficult to separate the target substance by the difference in the molecular size, by utilizing the difference in dissolution and/or diffusion in the membrane. Such a membrane is used, for example, as a reverse osmosis membrane for removing or concentrating inorganic salts having a size of an atomic or ionic level or as a pervaporation membrane for separation of low molecular compounds having a molecular size very close to each other. In designing such a membrane, efforts have also been directed to increasing the performance by densifying the surface pore size to 1.0 nm or less, making the membrane non-porous, and controlling the charge strength, and the like. For example, it has been reported that a sulfonated aromatic ether polymer membrane (refer to Non-patent Document 3) and an aminated aromatic ether polymer membrane (refer to Non-patent Document 4) exhibit excellent ion separating effects. However, since the sulfonated aromatic ether polymer membrane shows strong anionic properties and the aminated aromatic ether polymer membrane shows cationic properties during a liquid treatment using water as solvent, problems such as adsorption and denaturation occur depending on the materials to be treated. Moreover, the aromatic ether polymer must be chemically modified in order to introduce a charge structure and the like. This may cause problems such as reduction of physical strength, a decrease in solvent resistance, and the like.

When a membrane provided for the treatment of liquid, which is as important as the gas separation membrane, is considered, size of the material to be separated is generally 2.0 nm or more (refer to Non-patent Document 1). The major mechanism of separation that is applied is thus size separation. Therefore, in order to separate various materials to be separated in a liquid depending on their size, it is necessary to manufacture a porous membrane of which the pore size is precisely controlled based on the size of the materials to be separated.

An aromatic polysulfone polymer is given as an excellent material used for a membrane for treating liquid. The aromatic polysulfone polymer has many good solvents which are miscible with water at about room temperature and it is possible to produce various membranes such as a flat membrane, a hollow fiber membrane and the like by using a wet-phase separation membrane formation (refer to Non-patent Document 1 and Patent Document 2). Moreover, since the aromatic polysulfone polymer resin can be molded by melt molding, it is also possible to produce various membranes by a melt casting/spinning method. That is, the aromatic polysulfone polymers have large flexibility of membrane manufacturing, and membranes with a required pore size can be freely manufactured.

On the other hand, an aromatic ether polymer has scarcely been used as a membrane for treating liquid. The melting point of the aromatic ether polymer is very close to the thermal decomposition temperature in comparison with an aromatic polysulfone polymer. Thus, it has been difficult to use the aromatic ether polymer for manufacturing a membrane by a melt casting/spinning method in which sufficient melting is indispensable while inhibiting decomposition of resin. In addition, an aromatic ether polymer having high solvent resistance, differing from the aromatic polysulfone polymer in solubility to organic solvents, does not have a good solvent miscible with water, which is commonly used as a coagulating liquid, at around room temperature. Ultrafilter membranes made from an aromatic ether polymer which have been reported heretofore were manufactured by a method of using a casting/spinning solution of which a good solvent is a halogen-containing non-aqueous organic solvent (refer to Non-patent Document 5). Such a method has been difficult to carry out industrially due to a heavy environmental load and high production cost. Manufacture of membrane from an aromatic ether polymer by a wet-phase separation membrane formation using a halogen-free aqueous organic solvent at around room temperature has also been very difficult. Furthermore, it is very difficult to obtain a stable and homogeneous casting/spinning solution by blending a hydrophilic polymer as a hydrophilizing agent to the casting/spinning solution for the wet-phase separation membrane formation containing aromatic ether polymer, because the solubility of the aromatic ether polymer is decreased.

In respect of performance, the high hydrophobic property of the aromatic ether polymer is a problem when the aromatic ether polymer is used as a membrane for using water or a water-soluble organic solvent such as an aqueous solution or an alcohol as a filtering solvent or when the aromatic ether polymer is used for separating proteins.

[Patent Document 1] JP-A-03-65227
[Patent Document 2] Japanese Patent No. 2782583
[Non-patent Document 1] Membrane Technology (2nd edition), IPC, edited by Marcel Mulder, supervised and translated by Masakazu Yoshikawa, Tsuyoshi Matsuura, and Tsutomu Nakagawa (1997), pp. 16, 45-51, 256, 275-280
[Non-patent Document 2] Journal of Membrane Science Vol. 116, pp. 171-189, 1996: S. Berghmans, J. Mewis, H. Berghmans, H. Meijer
[Non-patent Document 3] Desalination, Vol. 155, pp. 229-242, 2003: Isabelle M. Noel, Remi E, Lebrun, Christian R. Bouchard
[Non-patent Document 4] Journal of Membrane Science Vol. 215, pp. 25-32, 2003: Xu Tongwen, Yang Weihua
[Non-patent Document 5] Desalination, Vol. 22, pp. 205-219, 1977: L. Broens, D. M. Koenhen, C. A. Smolders

DISCLOSURE OF THE INVENTION

Problems to be Solved by the Invention

In recent years, demand for a membrane using for separation in a membrane field for treating liquid has been upgrading increasingly.
In particular, in purification and separation of medical treatment, medicines, foods and beverages which demand high purity and safety, treatment with high energy radiation such as γ-ray radiation and the like is widely and increasingly used as a sterilizing method being simple, low cost and reliable.
As a result, a hydrophilized membrane for treating liquid having higher resistance to high-energy rays than the conventional aromatic polysulfone polymer has been desired.

Means for Solving the Problems

The inventors of the present invention have closely studied an aromatic ether polymer to achieve the above object. However, since the aromatic ether polymer possesses high solvent resistance, there has been no good solvent miscible with water at around room temperature for the aromatic ether polymer. The aromatic ether polymer thus could not be formed into a membrane by a wet-phase separation membrane formation at around room temperature. In addition, differing from the aromatic polysulfone polymer, the melting point of the aromatic ether polymer is very close to the thermal decomposition temperature. Thus, it has been also difficult to use the aromatic ether polymer for manufacturing a membrane by a melt casting/spinning method in which it is essential to sufficiently melt the resin while inhibiting decomposition.
Furthermore, in respect of the performance, the aromatic ether polymer was unsuitable for use in liquid treatment using water or an aqueous organic solvent as a medium or in separation for proteins and the like due to the high hydrophobic properties.
The inventors of the present invention have conducted extensive studies. The inventors have found manufacturing conditions for a wet-phase separation membrane formation which can manufacture a membrane of an aromatic ether polymer using a halogen-free aqueous organic solvent and the manufacture of membranes from the aromatic ether polymer have become possible. As a result, the inventors have found a novel membrane for treating liquid, which has a controlled pore size and high water permeability, exhibits less deterioration due to sterilization with high energy rays, and be hydrophilized, can be obtained. These findings have led to the completion of the present invention.

Specifically, the present invention provides:
(1) A membrane for treating liquid comprising an aromatic ether polymer shown by the following formula (1), and being hydrophilized with a hydrophilizing agent;

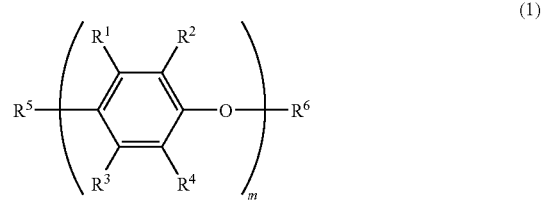

(wherein $R^1$, $R^2$, $R^3$, $R^4$, $R^5$, and $R^6$ represent hydrogen, an organic functional group having 1 to 6 carbon atoms, or a non-protonic organic functional group having 6 or less carbon atoms containing oxygen, nitrogen, or silicon, and these groups may be same or differ from each other, and m is the number of repeating units, and the polymer may be a copolymer containing two or more different repeating units).
(2) The membrane according to (1), wherein the hydrophilizing agent is nonionic.
(3) The membrane according to (1) or (2), wherein the hydrophilizing agent comprises a polyethylene glycol polymer and/or a polymer containing a segment derived from a polyethylene glycol polymer.
(4) The membrane according to (1) or (2), wherein the hydrophilizing agent comprises a block copolymer comprising a hydrophobic polymer and a nonionic hydrophilic polymer.
(5) The membrane according to any one of (1) to (4), wherein the hydrophilizing agent comprises a block copolymer comprising a hydrophobic polymer and a polyethylene glycol polymer.
(6) A membrane raw material comprising a polymer composition containing a polystyrene-polyethylene glycol block copolymer and an aromatic ether polymer shown by the following formula (1),

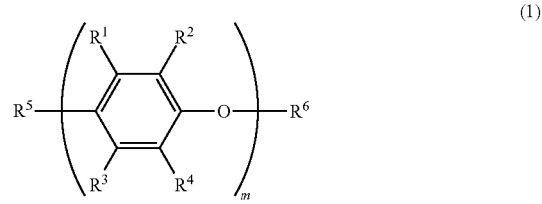

(wherein $R^1$, $R^2$, $R^3$, $R^4$, $R^5$, and $R^6$ represent hydrogen, an organic functional group having 1 to 6 carbon atoms, or a non-protonic organic functional group having 6 or less carbon atoms containing oxygen, nitrogen, or silicon, and these groups may be same or differ from each other, and m is the number of repeating units, and the polymer may be a copolymer containing two or more different repeating units).
(7) A membrane for treating liquid formed from the membrane raw material according to (6).
(8) The membrane according to any one of (1) to (5) and (7), wherein the hydrophilizing agent has a number average molecular weight of 500 to 50,000, or the hydrophilizing agent comprises a compound having a hydrophobic part and a hydrophilic segment, and the hydrophilic segment has a number average molecular weight of 500 to 50,000.

(9) The membrane according to any one of (1) to (5), (7), and (8), wherein the membrane is a flat membrane.

(10) The membrane according to any one of (1) to (5), (7), and (8), wherein the membrane is a hollow fiber membrane.

(11) The membrane according to any one of (1) to (5) and (7) to (10), wherein a water permeability of the membrane is $6.0 \times 10^{-7}$ (m$^3$/(hr·m$^2$·Pa)) or more.

(12) The membrane according to any one of (1) to (5) and (7) to (11), wherein a water permeability of the membrane is $10.0 \times 10^{-7}$ (m$^3$/(hr·m$^2$·Pa)) or more.

(13) The membrane according to any one of (1) to (5) and (7) to (12), wherein the membrane has no macrovoids therein.

(14) The membrane according to any one of (1) to (5) and (7) to (13), wherein the membrane is used for purification, concentration, or separation of medicines.

(15) The membrane according to any one of (1) to (5) and (7) to (13), wherein the membrane is used for purification, concentration, or separation of proteins and/or antibodies.

(16) The membrane according to any one of (1) to (5) and (7) to (13), wherein the membrane is used for a medical treatment including a blood treatment.

(17) The membrane according to any one of (1) to (5) and (7) to (13), wherein the membrane is used for preparation of foods and beverages.

(18) A method for preparing a membrane for treating liquid comprising an aromatic ether polymer shown by the following formula (1) by a wet-phase separation membrane formation using a halogen-free organic solvent as a good solvent for a casting/spinning solution,

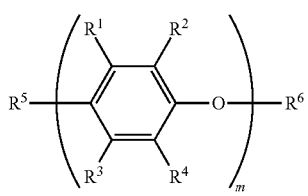

(1)

(wherein $R^1$, $R^2$, $R^3$, $R^4$, $R^5$, and $R^6$ represent hydrogen, an organic functional group having 1 to 6 carbon atoms, or a non-protonic organic functional group having 6 or less carbon atoms, containing oxygen, nitrogen, or silicon, and these groups may be same or differ from each other, and m is the number of repeating units, and the polymer may be a copolymer containing two or more different repeating units).

(19) The method according to (18), wherein as the good solvent for the casting/spinning solution, a halogen-free aqueous organic solvent is used.

(20) The method according to (18) or (19), wherein as the good solvent for the casting/spinning solution, one or more selected from N-methyl-2-pyrrolidone, N,N-dimethylacetamide, N,N-dimethylformamide, and γ-butyrolactone is used.

(21) The method according to any one of (18) to (20), wherein the casting/spinning solution contains a hydrophilizing agent.

(22) The method according to any one of (18) to (21), wherein a coagulating liquid contains water.

(23) The method according to any one of (18) to (22), wherein the coagulating liquid contains a polyol solvent shown by the following formula (2),

HO—R$^7$—OH (2)

(wherein R$^7$ represents an organic functional group having 1 to 20 carbon atoms or has a structure containing one or more oxygen atoms and 1 to 20 carbon atoms, and may contain one or more selected from a hydroxyl group, an ether bond, an ester group, a ketone group, and a carboxylic acid).

(24) The method according to any one of (18) to (23), wherein the coagulating liquid has at least a viscosity of 3 cp or more at 20° C.

(25) The method according to any one of (18) to (24), wherein the membrane-forming temperature is 80° C. or more.

(26) A module for treating liquid comprising a casing containing the membrane according to any one of (1) to (5) and (7) to (13).

Effect of the Invention

According to the present invention, a membrane for treating liquid made from a hydrophilized aromatic ether polymer, which has a controlled pores size and high water permeability, and exhibits less deterioration due to sterilization with high energy rays, can be provided. In addition, according to the present invention, as a method for manufacturing the membrane for treating liquid, a method for manufacturing the membrane by a wet-phase separation membrane formation using a halogen-free aqueous organic solvent can be provided. Furthermore, a module for treating liquid comprising the membrane for treating liquid can be provided.

BEST MODE FOR CARRYING OUT THE INVENTION

Figure 1:
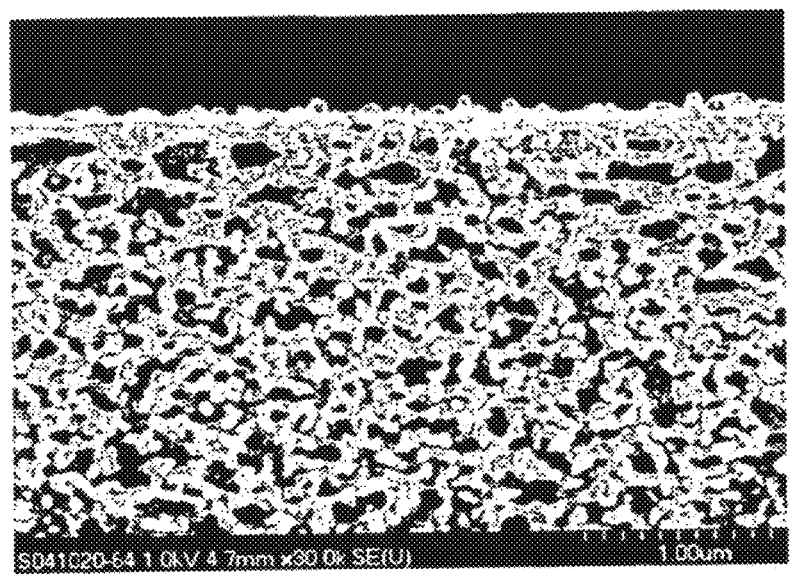
FIG. 1 is an SEM photograph of Example 1.

The present invention will be described in detail below.

The membrane for treating liquid of the present invention is a porous membrane used for separating a solid, liquid, or gas as a separation target substance from a mixed fluid to be separated which is liquid at the separating temperature, provided that a membrane having a pore size of 1 nm or less, of which the separation principle is not the size, and the separation target substance is dissolved and/or diffused in the membrane does not include within the scope of the separation membrane of the present invention. For example, a reverse osmosis membrane for removing or concentrating inorganic salts having a size of an atomic or ionic level and a pervaporation membrane for separating low molecular compounds having a molecular size very close to the others, do not include within the scope of the membrane for treating liquid of the present invention.

The aromatic ether polymer of the present invention is shown by the following formula (1).

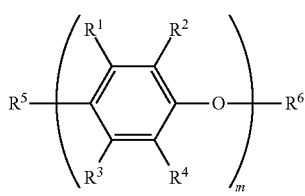

(1)

In the formula (1), $R^1$, $R^2$, $R^3$, $R^4$, $R^5$, and $R^6$ represent hydrogen, an organic functional group having 1 to 6 carbon atoms, or a non-protonic organic functional group having 6 or less carbon atoms, containing oxygen, nitrogen, or silicon, and these groups may be same or differ from each other. In the chemical structure m is the number of repeating units. The polymer may be a copolymer containing two or more different repeating units, insofar as the units have the structure shown by the formula (1). The phenolic hydroxyl group at the ends of the aromatic ether polymer of the present invention may be modified by esterification, etherification, epoxidation, or the like, if required, in order to maintain a pH at which the separation target substance can stably exist in the liquid. In addition, it is possible to introduce chemical structures such as an amino group, a monoalkylamino group, a dialkylamino group, a carboxyl group, and a sulfonyl group into the polymer ends, if required, in order to ensure compatibility with the electrostatic characteristics of the separation target substance.

The number average molecular weight of the aromatic ether polymer is, for example, 5,000 to 400,000. If the number average molecular weight is in this range, the polymer can be sufficiently dissolved in good solvents used for the membrane-forming process and a membrane with sufficient strength for use as a membrane for treating liquid can be obtained. A more preferable lower limit of the number average molecular weight is 8,000 or more, and particularly preferably 10,000 or more, and a more preferable upper limit is 200,000 or less, and particularly preferably 100,000 or less.

"Hydrophilization" in the present invention means increasing or providing hydrophilicity.

The "hydrophilizing agent" in the present invention is a compound to provide the aromatic ether polymer of the membrane material with hydrophilicity and improve contact of the liquid mixture to be subjected to separation treatment with the membrane for treating liquid made from an aromatic ether polymer of the present invention. In order to reduce an electric interaction with the target substance to be separated, the hydrophilizing agent is preferably a nonionic compound not containing a charge structure.

The hydrophilizing agent in the present invention may be either a low molecular compound or a polymeric compound. Specifically, diethylene glycol, polyethylene glycol, polypropylene glycol, polyethylene oxide, a polyethylene glycol-polypropylene glycol block copolymer, polyvinyl alcohol, polyacrylamide, poly-N,N-dimethylacrylamide, poly-N-isopropylacrylamide, polyvinylpyrrolidone, polyhydroxyacrylate, polyhydroxymethacrylate, carboxymethylcellulose, starch, corn starch, polychitosan, and polychitin can be given. Surfactants, block copolymers and graft copolymers containing these compounds as a hydrophilic segment can also be used as the hydrophilizing agent. A polystyrene-polyethylene glycol block copolymer possesses polyethylene glycol which has a high hydrophilicity as a hydrophilic segment, thus can be effectively used as a hydrophilizing agent in the present invention. These compounds may be used in combination of two or more. Among them, particularly suitable compounds are polyethylene glycol, and block copolymers and graft copolymers containing polyethylene glycol as a hydrophilic segment. Furthermore, polystyrene-polyethylene glycol block copolymer can be particularly suitably used as a hydrophilizing agent to increase the hydrophilicity of the aromatic ether polymer membrane.

The molecular weight of the hydrophilizing agent in the present invention is appropriately selected depending on the production method and its condition. For example, when the membrane is produced by a wet-phase separation membrane formation using a halogen-free water soluble organic solvent, the solubility of the aromatic ether polymer having a high solvent resistance is very low. For this reason, when blending the hydrophilizing agent and the casting/spinning solution, the molecular weight and the addition amount of the hydrophilizing agent must be suitably selected in order to obtain a casting/spinning solution in which the hydrophilizing agent is homogeneously dissolved. In order to use the hydrophilizing agent of a sufficient addition amount, the molecular weight of the hydrophilizing agent, in terms of the number average molecular weight, is 300 to 100,000, for example. The hydrophilizing agent with the molecular weight in this range can be sufficiently dissolved in a good solvent used for membrane-forming. A more preferable lower limit is 400 or more, and particularly preferably 500 or more, and a more preferable upper limit is 70,000 or less, and particularly preferably 50,000 or less.

When the hydrophilizing agent in the present invention is a compound comprising a hydrophobic part and a hydrophilic segment, the number average molecular weight of the hydrophilic segment of the hydrophilizing agent is preferably from 300 to 100,000. The hydrophilizing agent in which the hydrophilic segment has a molecular weight in this range can be sufficiently dissolved in the good solvent used for membrane-forming. A more preferable lower limit is 400 or more, and particularly preferably 500 or more, and a more preferable upper limit is 70,000 or less, and particularly preferably 50,000 or less.

The polystyrene-polyethylene glycol block copolymer in the present invention is a block copolymer comprising a segment derived from polystyrene and a segment derived from polyethylene glycol.

As the polystyrene polymer forming the segment derived from the polystyrene polymer of the polystyrene-polyethylene glycol block copolymer used in the present invention, a polystyrene polymer comprising the repeating units shown by the following formula (3) is preferable. In the following formula (3), $R^8$, $R^9$, $R^{10}$, $R^{11}$, $R^{12}$, $R^{13}$, $R^{14}$, and $R^{15}$ represent hydrogen, a halogen atom excluding fluorine, an organic functional group having 1 to 6 carbon atoms, or a functional group having 6 or less carbon atoms and containing oxygen, nitrogen, or silicon, and these groups may be same or differ from each other. In the formula (3), l is the number of repeating units. The polymer may be a copolymer containing two or more different repeating units, insofar as the units have the structure shown by the formula (3).

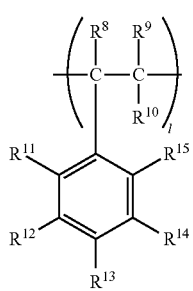

(3)

In the polystyrene-polyethylene glycol block copolymer used in the present invention, the number average molecular weight of the segment derived from polystyrene polymer is 300 to 1,000,000. If the number average molecular weight of the segment is in this range, the polymer can be sufficiently dissolved in the good solvent used for the membrane-forming, and the dissolution property of the polymer in an aqueous solution or an aqueous organic solvent can simultaneously be reduced. A more preferable lower limit is 500 or more, and particularly preferably 700 or more, and a more preferable upper limit is 50,000 or less, and particularly preferably 30,000 or less.

As the polyethylene glycol polymer forming the segment derived from the polyethylene glycol polymer of the polystyrene-polyethylene glycol block copolymer used in the present invention, a polyethylene glycol polymer comprising the repeating unit shown by the following formula (4) and/or the repeating unit shown by the following formula (5) is preferable. In the formula (5), $R^{16}$ is an organic functional group having 3 or more, and less than 30 carbon atoms. $R^{16}$ may contain an ether group, an ester group, a hydroxyl group, a ketone group, or a carboxylic acid group, unless the hydrophilicity is not significantly reduced. n and o are the numbers of repeating units.

(4)

(5)

In the polystyrene-polyethylene glycol block copolymer used in the present invention, the number average molecular weight of the segment derived from polyethylene glycol polymer is 300 to 100,000. If the number average molecular weight of the segment is in this range, the polymer can be sufficiently dissolved in the good solvent used for the membrane-forming and sufficient hydrophilicity can simultaneously be obtained. A more preferable lower limit is 400 or more, and particularly preferably 500 or more, and a more preferable upper limit is 70,000 or less, and particularly preferably 50,000 or less.

As to the ratio of the segment derived from polystyrene polymer to the segment derived from polyethylene glycol polymer in the polystyrene-polyethylene glycol block copolymer used in the present invention, the ratio of the segment derived from polystyrene polymer to the total polystyrene-polyethylene glycol block copolymer is 10 to 99 wt %. The polystyrene-polyethylene glycol block copolymer having the above ratio may exhibit sufficient hydrophilicity, while inhibiting dissolution. A more preferable lower limit is 20 wt % or more, and particularly preferably 30 wt % or more, and a more preferable upper limit is 98 wt % or less, and particularly preferably 97 wt % or less.

The polystyrene-polyethylene glycol block copolymer in the present invention may be a di-block copolymer consisting of two pairs of said segment, a tri-block copolymer consisting of three pairs of said segment, or a tetra-block copolymer consisting of four pairs of said segment. The polystyrene-polyethylene glycol block copolymer may also be a mixture of two or more of these block copolymers. The number average molecular weight of each segment forming the block copolymer may be either the same or different.

The segment derived from polystyrene polymer and the segment derived from polyethylene glycol polymer in the polystyrene-polyethylene glycol block copolymer used in the present invention must be directly bonded at the polymer ends. If necessary for production, a low molecular compound and/or an organic functional group may be used as a spacer to connect the segment derived from polystyrene polymer and the segment derived from polyethylene glycol polymer. In the case where the number average molecular weight of the low molecular compound and/or the organic functional group is not more than 500, the effects of the segment derived from polystyrene polymer and the segment derived from polyethylene glycol polymer can be expressed without reduction. Specifically, a low molecular compound formed between polystyrene and polyethylene glycol when the polyethylene glycol is condensed after polymerizing styrene using a radical polymerization initiator having a reactive functional group and the like can be given.

As an example of the method for producing the polystyrene-polyethylene glycol block copolymer in the present invention, a method of using a radical polymerization initiator which has a reactive functional group can be given. Specifically, polystyrene having an acid chloride group at the end can be obtained by radically polymerizing styrene after chemically converting a carboxylic acid group into an acid chloride group using an azo radical polymerization initiator having a carboxylic-acid group. Then, polyethylene glycol is condensed to obtain a polystyrene-polyethylene glycol block copolymer (KOBUNSHI RONBUNSHU (Japanese Journal of Polymer Science and Technology), 1976, Vol. 33, p. 131). The polystyrene-polyethylene glycol block copolymer can also be obtained by radically polymerizing styrene using an azo polymerization initiator containing polyethylene glycol units. As an alternative example of synthetic method, a method of using living polymerization can be given. Specifically, styrene is polymerized by living radical polymerization using a nitroxide compound to obtain a polymer having the nitroxide compound combined at the end thereof. Then, the polymer end is converted into a hydroxyl group by hydrolysis, and a coupling reaction with polyethylene glycol is carried out to obtain a polystyrene-polyethylene glycol block copolymer (Polymer, 1998, Vol. 39, No. 4, p. 911).

As the method for hydrophilizing the membrane for treating liquid made from the aromatic ether polymer using the hydrophilizing agent in the present invention, a blending method of mixing the hydrophilizing agent before membrane-forming, a coating method of dipping the membrane in a solution containing the hydrophilizing agent and drying the solution to allow the hydrophilizing agent to remain on the membrane surface, a method of graft-copolymerizing a hydrophilic acrylic monomer, methacrylic monomer, acrylamide monomer, or the like onto the membrane surface, and the like can be given. Two or more of these methods may be used in combination. The blending method or the coating method is preferable, because the aromatic ether polymer is not chemically modified. From the aspect of manufacturing, the blend method in which the hydrophilization treatment can be carried out in one step is preferable.

The wet-phase separation membrane formation can be given as a specific example of manufacturing the membrane for treating liquid made from the aromatic ether polymer of the present invention. The wet-phase separation membrane formation is a method of obtaining a membrane by causing a casting/spinning solution in which the membrane material is dissolved in a good solvent to come in contact with a coagulating liquid, which is miscible with the good solvent in the casting/spinning solution, but is not compatible with the membrane material, to cause phase separation induced by concentration difference from the contact surface to occur.

When using the aromatic ether polymer with high solvent resistance, finding optimal manufacturing conditions was a very important subject in order to constantly obtain a homogeneously dissolved casting/spinning solution and to form the membrane.

Any solvent that can stably dissolve 5 wt % or more of the aromatic ether polymer of the membrane material under the membrane-forming conditions can be used as a good solvent in the wet-phase separation membrane formation for obtaining the membrane of the present invention. From the aspect of the environment and cost, a halogen-free aqueous organic solvent is preferably used. An aqueous organic solvent in the present invention refers to a solvent dissolvable in an amount of 10 g or more in 100 g of purified water at 20° C., and preferably miscible with water. Specifically, N-methyl-2-pyrrolidone, N,N-dimethylacetamide, dimethylsulfoxide, N,N-dimethylformamide, and γ-butyrolactone can be given. These aqueous organic solvents may be used in combination of two or more.

As an example of the casting/spinning solution used for the wet-phase separation membrane formation for obtaining the polymer membrane of the present invention, a solution in which a hydrophilizing agent is homogeneously dissolved in a good solvent, in an amount of 0.1 wt % or more, preferably 0.5 wt % or more, and particularly preferably 1 wt % or more, but not more than 45 wt %, preferably not more than 35 wt %, and particularly preferably not more than 25 wt %, can be given.

The amount of the aromatic ether polymer in the casting/spinning solution (100 wt %) is 1 wt % or more as lower limit, preferably 2 wt % or more, and particularly preferably 3 wt % or more, but not more than 45 wt % as upper limit, preferably not more than 35 wt %, and particularly preferably not more than 25 wt %. A casting/spinning solution in which these components are homogeneously dissolved is preferably used.

The temperature of the casting/spinning solution which can be used is 25° C. or more as lower limit, preferably 65° C. or more, and particularly preferably 80° C. or more, but not more than the boiling point of the good solvent in the casting/spinning solution as upper limit. This range of temperature can increase the solubility of the aromatic ether polymer and ensures the viscosity of the casting/spinning solution suitable for producing the membrane.

The coagulating liquid used in the wet-phase separation membrane formation for obtaining the membrane of the present invention refers to a fluid which causes concentration-induced phase separation when contacting with the casting/spinning solution and forms a membrane from the contact surface. Specifically, purified water, a monohydric-alcohol solvent, a polyol solvent shown by the following formula (2), and a mixture of two or more thereof are preferably used.

HO—R$^7$—OH    (2)

In the formula (2), R$^7$ represents an organic functional group having 1 to 20 carbon atoms or a structure containing one or more oxygen atoms and 1 to 20 carbon atoms, and may contain one or more selected from a hydroxyl group, an ether bond, an ester group, a ketone group, and a carboxylic acid. As an example of the polyol solvent shown by the formula (2), ethylene glycol, diethylene glycol, triethylene glycol, tetraethylene glycol, glycerol, propylene glycol, 1,2-butanediol, 1,4-butanediol and the like can be given.

It is possible to control water permeability by the viscosity of the coagulating liquid used in the wet-phase separation membrane formation for obtaining the membrane for treating liquid. It was found that high viscosity of the coagulating liquid moderates permeation of the coagulating liquid into the casting/spinning solution, thereby improving the water permeation performance of the resulting membrane. Moreover, the coagulating liquid with a high viscosity has an effect of preventing formation of macrovoids in the resulting membrane. The viscosity of the coagulating liquid is preferably 3 cp or more at 20° C. in order to obtain higher water permeability performance. The viscosity is more preferably 5 cp or more. A water-soluble polymer such as polyvinyl alcohol, polyethylene glycol, polypropylene glycol, polyethylene oxide, a polyethylene glycol-polypropylene glycol block copolymer, polyacrylamide, polyvinylpyrrolidone, polyhydroxyacrylate, polyhydroxymethacrylate, polyacrylic acid, polymethacrylic acid, polyitaconic acid, polyfumaric acid, polycitraconic acid, poly-p-styrene sulfonic acid, sodium poly-p-styrene sulfonate, N,N-dimethylacrylamide, carboxymethylcellulose, starch, corn starch, polychitosan, and polychitin may be added to the coagulating liquid to increase the viscosity. The addition of a high viscosity solvent with a viscosity of 5 or more cp at 20° C., such as the above-mentioned polyol solvent is also preferable.

It is also possible to add a good solvent such as N-methyl-2-pyrrolidone, N,N-dimethylacetamide, dimethylsulfoxide, N,N-dimethylformamide, and γ-butyrolactone and the like to the coagulating liquid. In the case of using a coagulating liquid particularly containing a good solvent in a non-solvent, although the composition varies depending upon the composition of the casting/spinning solution, the contact temperature of the casting/spinning solution with the coagulating liquid, and the like, the amount of the good solvent in 100 wt % of the coagulating liquid is preferably 0 wt % or more, but not more than 90 wt %. If the composition is in this range, the concentration-induced phase separation is sufficiently attained, with a necessary and sufficient degree required for forming a membrane in the coagulating liquid used in the wet-phase separation membrane formation for manufacturing the membrane for treating liquid of the present invention.

The viscosity of the coagulating liquid in the present invention is a value measured by using a glass capillary viscometer. Specifically, the coagulating liquid is placed in a glass capillary viscometer adjusted to a fixed temperature in a thermostat water bath at 20° C. and allowed to stand for 30 minutes or more until the temperature becomes constant, then a kinematic viscosity is measured. The viscosity of the coagulating liquid can be calculated by applying the resulting kinematic viscosity value to the following equation. The Ubbelohde viscometer (manufactured by Shibata Scientific Technology Ltd.) or the like may be used as the glass capillary viscometer.

$$v = \eta/\rho$$

(wherein v) represents kinematic viscosity (mm$^2$/s), η represents viscosity (cp), and ρ represents density (g/cm$^3$)).

The membrane-forming temperature in the wet-phase separation membrane formation in the present invention refers to a temperature at which the casting/spinning solution is caused to come into contact with the coagulating liquid to cause the concentration-induced phase separation. Such a temperature is determined according to the temperature of the double spinneret used if the membrane is the hollow fiber membrane of the present invention. In the case of a flat membrane, the membrane-forming temperature is determined according to the coagulating liquid temperature. The lower limit of the membrane-forming temperature is 25° C. or more, preferably 80° C. or more, and particularly preferably 90° C. or more. The upper limit of the membrane-forming temperature is not more than the boiling point of the casting/spinning solution or the coagulating liquid, preferably at least 5° C.

lower than the boiling point, and particularly preferably at least 10° C. lower than the boiling point.

A particularly high-strength membrane can be obtained when the casting/spinning solution is caused to come in contact with the coagulating liquid at a temperature of the membrane-forming temperature of 80° C. or more and at least 10° C. lower than the boiling point of the casting/spinning solution or the coagulating liquid.

After homogeneous dissolution of the components, it is desirable to remove dissolved gas from the casting/spinning solution and the coagulating liquid used for the wet-phase separation membrane formation for obtaining the membrane for treating liquid of the present invention, particularly the coagulating liquid which is caused to flow inside the fibers in the manufacture of hollow fiber membrane (hereinafter referred to as "internal coagulating liquid"). The removal of dissolved gas can remarkably improve the defects of membrane due to bubbling of the dissolved gas. Particularly removal of oxygen gas reduces oxidation reactions of the materials during membrane processing at a high temperature.

In order to accelerate coagulation of the casting/spinning solution discharged from the double spinneret with the internal coagulating liquid when a hollow fiber membrane is manufactured by the wet-phase separation membrane formation of the present invention, a vessel (a coagulating vessel) may be installed immediately below the spinneret to cause the casting/spinning solution to come in contact with the coagulating liquid filled When a hollow fiber membrane is manufactured by the wet-phase separation membrane formation of the present invention, the distance from the spinneret to the surface of the external coagulating liquid (hereinafter referred to as "air gap") and the temperature and humidity in the space from the spinneret to the internal coagulating liquid surface may be adjusted in order to freely control the cross-sectional structure of the hollow fiber membrane, including not only a uniform structure, but also various asymmetric structures.

The lower limit of the air gap is 0.01 m, preferably 0.05 m, and particularly preferably 0.1 m or more, and the upper limit is 2.0 m, preferably 1.5 m, and particularly preferably 1.2 m or less. The lower limit of the temperature of the space from the spinneret to the internal coagulating liquid surface is 20° C. or more, preferably 50° C. or more, and particularly preferably 80° C. or more. Although the humidity varies depending on the temperature, the lower limit is 0%, preferably 25%, and particularly preferably 50% or more, and the upper limit is 100% or less.

Although the spinning speed when manufacturing a hollow fiber membrane by the wet-phase separation membrane formation of the present invention may vary depending on various factors of the manufacturing conditions, such as the form of the spinneret, the composition of the spinning solution, the compositions of the internal and external coagulating liquid, the temperatures of the spinning solution and coagulating liquids, and the like, said speed is generally selected from a range of 600 m/hour to 9,000 m/hour.

A fine porous membrane with sufficient strength and ductility can be obtained by using the wet-phase separation membrane formation of the present invention. In addition, a porous membrane having a gradient structure, which can be obtained only with difficulty in the melt casting/spinning method using the temperature-induced phase separation, can be easily manufactured by using the concentration-induced phase separation in the wet-phase separation membrane formation of a present invention, and it is possible to provide the resulting membrane with high water permeability.

In the wet-phase separation membrane formation of the present invention, it is possible to accelerate solvent removal by immersing the membrane in a solvent removing medium after coagulation with a coagulating liquid in order to increase the hardness of the membrane. The solvent removing medium is a medium which can remove the solvent remaining after the concentration-induced phase separation using the coagulating liquid. Any solvent which does not dissolve the membrane can be used as solvent removing medium. In general, water, ethanol, and the like are used in many cases.

The membrane-forming temperature in the wet-phase separation membrane formation of the present invention refers to a temperature at which the casting/spinning solution is caused to come into contact with the coagulating liquid to effect the concentration-induced phase separation. The membrane-forming temperature is determined according to the temperature of the casting/spinning solution, the temperature of the coagulating liquid, the temperature of the double spinneret when the membrane is a hollow fiber membrane, the temperature of a metal plate to support the membrane when the membrane is a flat membrane, and the like. The lower limit of the membrane-forming temperature is 20° C. or more, preferably 25° C. or more, and particularly preferably 30° C. or more. The upper limit of the membrane-forming temperature is not more than the boiling point of the casting/spinning solution or the coagulating liquid, preferably at least 5° C. lower than each boiling point, and particularly preferably at least 10° C. lower than boiling points. A particularly high strength membrane can be obtained especially when the casting/spinning solution is caused to come in contact with the coagulating liquid at 80° C. or higher of the membrane-forming temperature and at least 10° C. lower than the boiling point of the casting/spinning solution or the coagulating liquid.

The undried membrane for treating liquid of the present invention obtained by the wet-phase separation membrane formation is dried at a temperature which the membrane does not break, for example, at a temperature in a range from 20° C. to a temperature not more than the melting point of the aromatic ether polymer. The drying temperature is preferably 50° C. to 150° C., more preferably 60° C. to 140° C., and particularly preferably 70° C. to 130° C. The drying time is determined in relation to the drying temperature, and may be roughly selected from a range of about 0.01 to 48 hours.

Although there are no specific limitations to the form of the membrane for treating liquid of the present invention, a flat membrane and a hollow fiber membrane can be given as typical examples.

The macrovoid in the present invention is a rough large pore in the membrane structure with a long diameter of 10 μm or more, that is, a pore of which the long diameter is 10 μm or more when the membrane cross-section is inspected using an electron microscope. The membrane which does not have macrovoids is useful in the application as a membrane for treating liquid, because liquid remains or stays in the membrane only with difficulty during treatment and separation, and such a membrane also produces almost no defects even during a high pressure operation. The presence or absence of macrovoids in the membrane in the present invention can be confirmed whether the macrovoids exist in $1.0 \times 10^{-2}$ mm² of the membrane cross-section or not when observing the membrane cross-section through an electron microscope. The macro voids are judged not to exist, if the number of macrovoids discovered after repeating the observation ten times is five or less.

The membrane for treating liquid of the present invention can be used for any application of treating liquid for size separation. A particularly suitable application is a filter using medical application, pharmaceutical application, food and beverage application, and relevant application thereof. Specifically, various filters used for medical application such as various blood purification application including plasma filtration, virus removal, and hemodialysis; various process filters used for medical application such as purification process for synthetic pharmaceuticals such as an anticancer drug and antibiotics, purification process for highly-purified amino acids for drugs, and purification process for antibody relevant pharmaceutical such as a polyclonal antibody and a monoclonal antibody; and various process filters used for food production application such as filters used when manufacturing of drinks and beverages, for example, sake, beer, wine, sparkling wine, tea, oolong tea, vegetable juice, and fruit juice can be given. The membrane of the present invention can also particularly be used as a process filter for removing aggregates from immunoglobulin which is an antibody pharmaceutical. The blood treatment application in the present invention refers to a blood treatment application such as purification of blood and the like, for example, the plasma filtration filter, the virus removing filter, the hollow fiber filter for hemodialysises included in the above-mentioned medical application can be given.

The membrane for treating liquid made from the aromatic ether polymer having porosity of the present invention possesses performance usable as a filter of the category generally called an ultrafilter membrane or a microfiltration membrane.

Water permeability in the present invention is indicated by the volume of water permeated during a unit period of time per unit area under unit pressure, provided that in the case that the water having a coefficient of viscosity of 0.0008902 (Pa·s), that is, water at 25° C., is caused to penetrate the membrane.

Among the membranes for treating liquid made from the aromatic ether polymer having porosity of the present invention, a hydrophilized membrane for treating liquid having a water permeability of $6.0 \times 10^{-7}$ ($m^3/(hr \cdot m^2 \cdot Pa)$) or more is very useful as an ultrafilter membrane.

The module for treating liquid of the present invention comprises, for example, a casing containing a flat membrane or a hollow fiber membrane therein, having at least one or more inlet ports to feed the liquid containing the separation target substance thereto and one or more outlet ports to discharge the separated liquid therefrom.

The casing used for the module of the present invention is assembled from one or more casing parts.

The material of the casing parts when the casing using for the module of the present invention is assembled may be selected from a metal, glass, a thermoplastic resin, a thermosetting resin, and the like, as required. A suitable material is a thermoplastic resin having transparency to the extent that the inside of the casing can be observed from the outside. Specifically, as the thermoplastic resin polymethyl methacrylate, polystyrene, hard vinyl chloride resin, polyethylene terephthalate, polypropylene, a polystyrene butadiene copolymer, polycarbonate, polysulfone and the like can be given. Particularly preferable materials are transparent amorphous resins such as a polystyrene butadiene copolymer, polycarbonate, polysulfone and the like.

The method for manufacturing the casing parts using when assembling the casing for the module of the present invention may be any method that can process one or more materials. For example, welding, press molding, injection molding, reaction injection molding, ultrasonic bonding, plasma bonding, adhesion using an adhesive, and the like can be given. These methods may be used either alone or in combination of two or more. A particularly preferable method for manufacturing the casing parts is a method of sealing injection molded articles made from a thermoplastic resin having transparency with a suitable adhesive.

The surfaces of the casing and/or casing parts used for the module of the present invention which do and/or do not come in contact with the liquid to be treated for separation may be subjected to surface treatment during and/or after molding or during and/or after assembly.

As the method of surface treatment, the surface may be applied with a hydrophilizing agent or oxidized by plasma treatment in air in order to hydrophilize the surface, the surface may be applied with a water-repelling agent and/or a releasing agent in order to hydrophobicize the surface, and the surface may be coated with various inorganic coating materials such as a silicon dioxide film by vapor deposition method or the like in order to decrease penetration of oxygen. Hydrophilizing treatment of the casing and/or the casing material makes it easy to control adhesion of the same and/or different materials in the interface during assembly of the module. Hydrophobicizing treatment improves release property of various protective films temporarily used during assembly.

The structure of the module of the present invention differs according to the form of the membrane to be used or the separation target substance in the liquid. For example, in the case the separation target substance is separable according to the size by using flat membrane, the module has a structure having one sheet of flat membrane or two or more sheets of flat membranes placed properly in the casing so that the liquid to be treated for separation flows only through these membranes, and a fluid inlet port is provided upstream of the flow path and an fluid outlet port downstream of the flow path. It is also possible to place in the casing and to assemble the module by combining the flat membrane with a holding material to hold the flat membrane such as a metal mesh and a nonwoven fabric. Furthermore, the flat membrane may be folded in the shape of a pleat when placed in the casing in order to increase the membrane area per unit volume of the casing.

If the membrane of the present invention is a hollow fiber membrane, and the separation target substance in the liquid to be treated is separated by utilizing the separation principle that a diffusion coefficient of the separation target substance different from that of the other substances, the method of manufacturing the module and the structure thereof are as follows.

A casing central part equipped with branched tubes to function as an inlet port and an outlet port in the vicinities of both ends and a casing cover equipped with branched tubes to function as an inlet port and an outlet port are provided as parts of the casing. The hollow fiber bundle having the number of the fibers from which a required membrane area is obtained is inserted into the casing central part, the space between the hollow fibers and the space between the hollow fibers and the casing central part are sealed while hollows of the hollow fibers are not blocked, and then the casing cover is connected to the casing central part in a manner so that the hollows of the hollow fibers are not blocked. Thereby, a module is obtained. In this module, an inlet port and an outlet port which allow liquid to flow only outside each hollow fiber, and an inlet port and an outlet port which allow liquid to flow only inside each hollow fiber are separately provided on the casing respectively. The module has a structure that liquid can be separated only through the hollow fiber membrane.

The membrane and the module for treating liquid of the present invention can be sterilized using any sterilization method. The high energy radiation sterilization using γ-rays or electron beams is preferably used, with a particularly preferable sterilization method being sterilization using γ-rays.

In order to maintain high safety to the human body when applying the separation membrane of the present invention to medical use, pharmaceutical use, and food and beverage use, particularly to a blood treatment use, it is demanded to decrease the deterioration of the materials of liquid separation membrane and to reduce elution accompanying the deterioration of such materials than before. A major factor causing deterioration of the materials in the above various applications is sterilization. Sterilization by high energy radiation using γ-rays frequently used in the application for blood treatment is particularly a major factor of the material deterioration, including discoloration and decreases of tensile strength and ductility (cf. Keizo Makuuchi, "Radiation processing of polymers" Rubber Digest Company, 2000). Therefore, it is very important that the membrane material have high γ-ray resistance.

EXAMPLES

The present invention is described below in more detail by way of Examples and Comparative Examples.

Membrane Preparation Example 1

Preparation of Flat Membrane 1.6 g of poly(2,6-dimethylphenylene-1,4-oxide) (Sigma Aldrich Japan, Inc., hereinafter abbreviated as "PPE") and 0.4 g of a hydrophilizing agent were added to 8.0 g of N-methyl-2-pyrrolidone (first grade reagent with a purity of 97%, Wako Pure Chemical Industries, Ltd., hereinafter abbreviated as "NMP"), and the mixture was heated and dissolved at 160° C. for one hour. Thereafter, a polymer solution at 90° C. was obtained. The polymer solution was gently dropped onto a glass plate heated at 90° C. and uniformly spread using an applicator, immediately followed by immersion into a coagulating liquid (purified water) heated at 90° C. The polymer precipitated at once to form a white flat membrane. The flat membrane was immersed in and washed with purified water at 90° C. five times, and dried using a hot air dryer at 70° C. for six hours.

When preparing a membrane for treating liquid with a different membrane structure, the composition ratio of PPE, the hydrophilizing agent, and the good solvent were appropriately changed.

Membrane Preparation Example 2

Preparation of Hollow Fiber Membrane 320 g of PPE and 110 g of hydrophilizing agent were added to 1,600 g of NMP, the mixture as a dispersion solution was poured into a $5,000 \times 10^{-6}$ m$^3$ reactor for the casting/spinning solution. A procedure of reducing the pressure to 0.02 MPa, followed by replacing the atmosphere with nitrogen while stirring the reactor was repeated five times. The internal temperature of the reactor was then increased to 160° C. to obtain a homogeneous NMP solution of PPE. At this stage, stirring was stopped and the internal temperature of the reactor was decreased to 90° C. over one hour, while maintaining the internal pressure of the reactor at 0.02 MPa as-is. Then, the internal pressure of the reactor was increased to atmospheric pressure with nitrogen to obtain a casting/spinning solution for spinning which was maintained at 90° C.

500 g of purified water was mixed with 500 g of NMP, and the mixture was added to a $3,000 \times 10^{-6}$ m$^3$ reactor for internal coagulating liquid. A procedure of reducing the pressure to 0.02 MPa, followed by replacing the atmosphere with nitrogen was repeated five times. After that, the internal temperature of the reactor was increased to 90° C., while maintaining the pressure at 0.02 MPa as-is. After one hour, the internal pressure of the reactor was increased to atmospheric pressure using nitrogen to obtain an internal coagulating liquid maintained at 90° C. to pass through hollow portions.

The internal coagulating liquid maintained at 90° C. was caused to flow through the inner hole of a double spinneret (inner diameter: 100 μm, slit width: 50 μm, and outer diameter: 300 μm) maintained at 90° C. at a flow rate of about $60 \times 10^{-6}$ m$^3$/hour to about $120 \times 10^{-6}$ m$^3$/hour, and then the casting/spinning solution maintained at 90° C. was caused to flow at a flow rate of $90 \times 10^{-6}$ m$^3$/hour to $240 \times 10^{-6}$ m$^3$/hour. The respective flow rates were suitably adjusted according to the wind-up speed during spinning.

The resulting hollow fiber membrane was introduced into an external coagulating liquid (purified water) in a coagulating vessel maintained at 90° C. through the air gap of 0.6 m to complete the coagulation, followed by winding-up by a winding device. The wind-up speed was from 2,400 m/hour to 4,800 m/hour.

The resulting hollow fiber membrane was immersed in and washed with purified water at 80° C. five times, and dried using a hot air dryer at 70° C. for six hours.

When preparing a membrane for treating liquid with a different membrane structure, the addition ratio of the components such as PPE, the hydrophilizing agent, the good solvent, the coagulating liquid, and the like were appropriately changed.

Preparation Example of Polystyrene-Polyethylene Glycol Block Copolymer

A $5,000 \times 10^{-6}$ m$^3$ reactor containing 2,400 g of xylene (Wako Pure Chemical Industries, Ltd.) was charged with 480 g of styrene (Wako Pure Chemical Industries, Ltd.) and 120 g of an azo polymerization initiator containing polyethylene glycol units ("VPE-0201," Wako Pure Chemical Industries, Ltd., the number average molecular weight of the polyethylene glycol segment portion: about 2,000). The reaction system was brought to a dry nitrogen atmosphere by bubbling dry nitrogen for 30 minutes or more, followed by polymerization reaction at 130° C. for seven hours. After cooling to room temperature, the reaction solution was gradually poured into excessive amounts of hexane (Wako Pure Chemical Industries, Ltd., special grade) to precipitate the polymer. The resulting polymer was washed three times with hexane, and dried at 50° C. under reduced pressure of 0.133 KPa for 24 hours to completely remove the residual solvent, monomers, and the like, thereby obtaining 409 g of white powder at an yield of 68 wt %.

When producing a polystyrene-polyethylene glycol block copolymer with a different composition ratio, the amount of styrene and the azo polymerization initiator containing polyethylene glycol units was appropriately changed.

Measuring Method

Method of Measuring the Membrane Thickness and Porosity of Flat Membrane

The thickness d of the flat membrane was measured using a micrometer manufactured by Mitutoyo Corp. (type IDF- 130). In determining the porosity of the flat membrane, the membrane was punched into a disk with a diameter of $25\times10^{-3}$ m, the weight was measured, and the volume was calculated from the area and the thickness of the disk. The results were applied to the following formula (6) to determine the porosity, wherein the bulk density of PPE was 1.06 and the bulk density of polysulfone ("P-1700," Solvay Advanced Polymers, K. K., hereinafter referred to as "PSf") was 1.24.

$$\text{Porosity } \alpha(\%) = (1-\text{weight}/(\text{density of resin} \times \text{volume of membrane})) \times 100 \quad (6)$$

Method of Measuring Thickness, Internal Diameter, and Porosity of Hollow Fiber Membrane The membrane thickness d and internal diameter of the hollow fiber membrane were measured using a laser beam microscope manufactured by Keyence Corp. ("VK9700"). In determining the porosity of the hollow fiber membrane, a bundle of 100 hollow fiber membranes was cut into a length of 0.2 m and weighed to determine the weight of one membrane. Then, the volume per one membrane was calculated from the internal diameter, the membrane thickness and the length of the hollow fiber membrane. The porosity was calculated using the above formula (6) in the same manner as the flat membrane.

Method of Measuring Water Permeability of Flat Membrane

The water permeability was calculated from the permeated amount of purified water in a low-pressure dead end filtration, the membrane area, the filtration pressure, and the filtration time. All operations relating to the measurement were carried out in a thermostatic chamber controlled at 25° C. First, the membrane was punched into a disk with a diameter of $25\times10^{-3}$ m, dipped in ethanol (Wako Pure Chemical Industries, Ltd.) for 0.05 hours and inserted into a plastic holder manufactured by ADVANTEC MFS, Inc. ("PP-25," effective filtration area: $3.5\times10^{-4}$ m$^2$). The plastic holder was connected to an acrylics tube, purified water at 25° C. was fed into the tube, and the tube was pressed by air with constant pressure (101325 Pa). The time T (hours) required for collecting $2\times10^{-6}$ m$^3$ of the filtrate was measured and applied to the following formula (7) to calculate the water permeability F.

$$\text{Water permeability } F(\text{m}^3/(\text{hr}\cdot\text{m}^2\cdot\text{Pa})) = \text{Volume of collected solution}(\text{m}^3)/(\text{Effective filtration area}(\text{m}^2) \times \text{Time}(\text{hours}) \times \text{Pressure}(\text{Pa})) = 2\times10^{-6}/(3.5\times10^{-4}\times T\times101325) \quad (7)$$

Method of Measuring Water Permeability of Hollow Fiber Membrane

All operations relating to the measurement were carried out in a thermostatic chamber controlled at 25° C. First, the membrane area per one hollow fiber membrane with a length of 0.2 m was calculated, and then the number of hollow fiber membranes forming a hollow fiber bundle with a membrane area of $1.00\times10^{-2}$ m$^2$ was determined.

The bundle having the above number of hollow fiber membranes was cut into a length of 0.3 m, and an epoxy sealing agent (a bond quick set 5 minute type, Konishi, Inc., main material: 2.0 g, curing agent: 2.0 g, acetone for viscosity adjustment (Wako Pure Chemical Industries, Ltd., special grade) 0.6 g) was coated from one end to the position depart 0.05 m from the end. The bundle was then inserted into a soft vinyl chloride tube with a length of 0.03 m (internal diameter: 6 mm, external diameter: 8 mm, hereinafter called "tube"). After curing for two hours, the other end was coated in the same manner with the epoxy sealing agent to the position of 0.05 m from the end, and the hollow fiber membrane was inserted into another tube so that the length of the hollow fiber membrane bundle between the both tubes at the ends was 0.2 m. After curing for two hours, the ends of the bundle were cut at the center of each tube to obtain a hollow fiber membrane for evaluation.

The fiber bundle for evaluation was dipped in ethanol for 0.05 hours and washed five times with purified water at 25° C. to remove the attached ethanol. After that, the fiber bundle for evaluation was immersed into purified water at 25° C. filled in a vat with a bottom area of 0.6 m×0.6 m and a height of 0.1 m, followed by attaching a plug to one end. The unplugged end of the tube was connected to a $20\times10^{-6}$ m$^3$ measuring pipette filled with purified water at 25° C., while the fiber bundle was immersed in the vat.

Air pressure of 26664 Pa was applied to the upper portion of the measuring pipette to cause the purified water at 25° C. to pass through the hollow fiber bundle. The time (hours) required for the water to permeate through from a scale of $10\times10^{-6}$ m$^3$ to $5\times10^{-6}$ m$^3$ of the measuring pipette was counted and the result was applied to the following formula (8) to calculate the water permeability F.

$$\text{Water permeability } F(\text{m}^3/(\text{hr}\cdot\text{m}^2\cdot\text{Pa})) = \text{Volume of permeated water}(\text{m}^3)/(\text{Membrane area of hollow fiber bundle}(\text{m}^2) \times \text{Permeation time}(\text{hours}) \times \text{Pressure}(\text{Pa})) = 5\times10^{-6}/(1.00\times10^{-2}\times T\times26664) \quad (8)$$

Measurement of Maximum Pore Diameter

All operations of the measurement were carried out in a thermostatic chamber controlled at 25° C. The bubble point method was used for measuring the maximum pore diameter of each membrane by filling all pores with distribution in the membrane with liquid and measuring the pressure required to replace the liquid with air. The pore diameter was determined by applying the surface tension of the liquid used for the measurement and the measured pressure to the Laplace's equation.

The specific measurement was carried out using the bubble point method pursuant to ASTM F316-86. In the case of a flat membrane, a membrane punched into a disk with a diameter of $25\times10^{-3}$ m was inserted into a flange-shaped membrane holder (effective filtration area: $3.5\times10^{-4}$ m$^2$), and immersed in liquid of a fluorocarbon (perfluoro carbon coolant "FX-3250" manufactured by Sumitomo 3M, surface tension at 25° C.: 10.47 mN/m). One side of a membrane was slowly pressed with air, and the pressure (Pa) at the time when the flow rate of the air permeating through the membrane reached $150\times10^{-6}$ m$^3$/hour was noted. The result was applied to the following formula (9) to calculate the maximum pore diameter. In the formula, B is a coefficient which is 2860 in the case of the following formula (9).

$$\text{Maximum pore diameter } (\mu m) = B \times \text{Surface tension of measurement liquid } (\text{mN/m})/\text{pressure } (\text{Pa}) = 2860\times10.47/P \quad (9)$$

The maximum pressure that could be applied to the membrane was 1.5 MPa because of the pressure resistance and safety of the measuring device. When gas did not permeate under the pressure of 1.5 MPa, the maximum pore diameter was deemed not to be measurable. In the case of a hollow fiber membrane, the inner surface area was calculated from the internal diameter of the hollow fiber, followed by calculating the length and the number of fibers when exhibiting the filtration area of $3.5 \times 10^{-4}$ m$^2$. Then, the required amount of the hollow fiber membrane calculated was filled into a cylindrical membrane holder, followed by measuring in the same manner as the flat membrane.

γ-Ray Irradiation Test Method

Each sample was sent to Radia Industry Co., Ltd., where the γ-ray irradiation test was carried out. In Radia Industry Co., Ltd., the samples of which the weight was measured were irradiated with γ-rays under two absorption dose conditions of 25 KGy and 57 KGy, using cobalt-60 as the γ-ray source at room temperature and under the atmosphere, while controlling the irradiation dose and time.

Color Difference Measuring Method

The discoloration of the material before and after γ-ray irradiation was measured using a color difference meter. An index L* of brightness of 25 KGy and 57 KGy, an index a* for red and green colors, and an index b* for yellow and blue colors were measured using a color difference meter (spectro-guide sphere gloss, BYK-Gardner), and differences Δa, Δb, and ΔL before and after irradiation were determined. A color difference E* was calculated using the following formula (10).

$$\text{Color difference } \Delta E^* = (\Delta a^2 + \Delta b^2 + \Delta L^2)^{0.5} \quad (10)$$

The larger the value of ΔE*, the larger the color difference before and after the irradiation.

Strength and Ductility Measuring Method

Deterioration of strength before and after γ-ray irradiation was confirmed. Tensile strength and ductility were measured in a thermostatic chamber at 25° C. using a tensile tester ("TG-1KNB", Minebea Co., Ltd., load cell: CHA-100-N-A558, strain rate: 10 mm/min).

Electron Microscope Measuring Method

A sample was cut to an appropriate size and secured to a sample table using a conductive tape, then carried out an osmium coating using a hollow cathode CVD osmium coater (type HPC-1S) manufactured by Vacuum Device Co. Ltd. The coated sample was used as a sample for electron microscope inspection. The surface and cross-section structure of the membrane were observed using a high resolution scanning electron microscope "S-4700" manufactured by Hitachi, Ltd. under the condition of an accelerating voltage of 1 kV, a working distance of $5 \times 10^{-3}$ m, and a predetermined magnification.

Calculation of Surface Coating Rate with Hydrophilizing Agent by X-Ray Photoelectron Spectroscopy (XPS) Measurement A sample was cut to an appropriate size, and subjected to the XPS measurement using "VG ESCALAB 250" manufactured by Thermo Electron Corp. under the condition of an AlKα line as an excitation source, an X-ray strength of 15 kV×10 mA, and an analysis area of about $1.0 \times 10^{-6}$ m$^2$. The surface coating rate of the hydrophilizing agent was calculated using the area intensity of the total carbon element at carbon 1s spectrum (bonding energy: 298 to 280 eV) and a peak area intensity originating from π-π* shake-up.

Specifically, the following formula (11) was used to calculate the surface coating rate of a polymer membrane comprising a hydrophilizing agent and an aromatic ether polymer. In the formula (11), D indicates the rate of the area intensity of π-π* shake-up in the total carbon element of the aromatic ether polymer which is a base material, E indicates the rate of the area intensity of π-π* shake-up in the total carbon element of the hydrophilizing agent, and F indicates the rate of the area intensity of π-π* shake-up in the total carbon element on the polymer membrane surface.

$$\text{Surface coating rate with hydrophilizing agent}(\%) = (D-F)/(D-E) \times 100 \quad (11)$$

In order to confirm the resistance to elusion property by ethanol, the membrane was immersed in ethanol for 24 hours, and subjected to measurement of the coating rate of the hydrophilizing agent on the surface of the polymer membrane after drying.

Gel Permeation Chromatography (GPC) Measurement

The number average molecular weight and the molecular weight distribution of the synthesized polystyrene-polyethylene glycol block copolymer were measured using "HLC-8020" apparatus manufactured by Tosoh Corp. equipped with GPC columns manufactured by Tosoh Corp. (TSKgel GMHHR-M×2). The measurement was conducted under the condition of the chloroform moving phase and a column temperature of 40° C. The number average molecular weight was calculated as a polystyrene-reduced molecular weight from the calibration curve produced using the elusion time of the standard polystyrene sample (Polymer Laboratories).

Nuclear Magnetic Resonance (NMR) Measurement

The composition ratio of the polystyrene-polyethylene glycol block copolymer was calculated by NMR measurement. The sample was dissolved in deuteriochloroform (manufactured by MERCK, tetramethylsilane content: 0.03%), and the NMR measurement was conducted at the observation nucleus $^1$H and an observation frequency of 400 MHz at room temperature using a JMM-LA400 apparatus manufactured by JEOL Ltd. The chemical shift was calculated taking the signal originating from tetramethylsilane to be 0 ppm. In particular, when the composition ratio of a copolymer comprising polystyrene and polyethylene glycol was calculated, the integration values of a signal originating from the benzene ring of polystyrene and the signal originating from the methylene group of polyethylene glycol were used.

Contact Angle Measurement

The contact angle of water was measured using an automatic contact angle meter (CA-V type) manufactured by Kyowa Interface Science Co., Ltd. Specifically, $1 \times 10^{-7}$ m$^3$ of purified water was dropped at an ambient temperature of 25° C., after 0.05 hours the contact angle was measured. The θ/2 method was used to calculate the contact angle.

Protein Adsorption Measurement

A 5% solution of bovine serum γ-globulin G (manufactured by Invitrogen) was filtered with a Planova 75N filter (manufactured by Asahi Kasei Pharma Corp.) to remove insoluble components, and diluted with a physiological saline solution (manufactured by Otsuka Pharmaceutical, Inc.) to a concentration of 40 μm/g to use as an IgG solution for the evaluation of protein adsorption property.

The hollow fiber membrane was previously immersed in ethanol for 24 hours, and washed by immersing in purified water for 24 hours. The sample was prepared so that the internal area of the membrane became $1.40 \times 10^{-3}$ m$^2$. Then, the hollow fiber membrane was cut to a length of 0.01 m, and the amount D (g) of water contained in the membrane was measured by measuring the weight. The membrane was put into a micro tube with a low protein adsorptivity (for $1.5 \times 10^{-6}$ m$^3$, manufactured by Hitec Co., Ltd.). An adsorption reaction was conducted by adding $1.4 \times 10^{-6}$ m$^3$ of the above IgG solution for evaluation into the micro tube and being allowed to stand at 25° C. for 20 hours.

$1.0 \times 10^{-6}$ m$^3$ of the supernatant liquid obtained after the adsorption reaction was sampled. The γ-globulin G (hereinafter abbreviated to IgG) concentration C (μg/g) of the sample was measured using Micro BCA Protein Assay Kit (manufactured by PIERCE). The amount of IgG adsorbed in the hollow fiber membrane was calculated by applying the values of the internal area of the membrane and the change of the IgG concentration in the IgG solution to the following formula (12).

$$\text{IgG adsorption}(\mu g/cm^2) = \{\text{IgG solution concentration before adsorption}(\mu g/g) \times \text{Added solution}(g) - \text{IgG solution concentration after adsorption}(\mu/g) \times [\text{Added solution}(g) + \text{Water in membrane}(g)]\} / \text{internal area of membrane}(cm^2) = 40 \times 1.4 - C \times (1.4 + D)/14 \qquad (12)$$

Evaluation of Protein Filtration Performance: IgG Monomer/Dimer Filtration

A 5% solution of bovine serum γ-globulin G (manufactured by Invitrogen) was filtered with a Planova 75N filter (manufactured by Asahi Kasei Pharma Corp.) to remove insoluble components, and diluted with a physiological saline solution (manufactured by Otsuka Pharmaceutical, Inc.) to a concentration of 10 mg/g to use as IgG solution for the evaluation of the protein filtration performance.

A hollow fiber bundle for evaluating protein filtration performance was prepared by using the production method of the hollow fiber bundle for evaluating the hollow fiber described in the measuring method of water permeability of the hollow fiber membrane using the number of hollow fibers to make a bundle having 0.833 mm$^2$ of a total cross-section area of the hollow portion of the hollow fiber bundle. The fiber bundle for evaluation of protein filtration performance was dipped in and washed with ethanol for 0.05 hours and washed five times with purified water at 25° C. to remove the attached ethanol. The resulting fiber bundle was subjected to the evaluation of protein filtration performance.

One end of the fiber bundle for evaluation of protein filtration performance was connected to a tube pump as an inlet side, and the other end was connected to a needle valve as an outlet side. The IgG solution for evaluation of protein filtration performance was caused to flow through the hollow fiber membrane at a linear velocity of 10 cm/sec using the tube pump, and the average pressure of the inlet side pressure and the outlet side pressure of the hollow fiber membrane was controlled to 26664 Pa by the needle valve. The filtrate sampling was started 0.417 hours after having begun to flow the IgG solution for evaluation of protein filtration performance, and the sample was collected for 0.083 hours.

The IgG solution was analyzed by HPLC (two G3000 SWXL columns, SC8020 system, and UV8020 detector, all manufactured by Tosoh Corp.) before and after the filtration to determine the permeation rates and the ratio of the permeation rates of the monomer and dimer of γ-globulin G (hereinafter abbreviated to IgG) from the ratio of the absorption peak area of UV 280 nm.

Example 1

A flat membrane was prepared according to the Membrane Preparation Example 1 by using PPE and polyethylene glycol (number average molecular weight: 4,000, Wako Pure Chemical Industries, Ltd., hereinafter referred to as "PEG") as a hydrophilizing agent.

The membrane thickness was 178 μm, porosity was 78%, water permeability was $35.0 \times 10^{-7}$ (m$^3$/(hr·m$^2$·Pa)), and the maximum pore diameter was 132 nm. The contact angle with water was 87°, and the surface coating rate of hydrophilizing agent of the membrane was 14%. The surface coating rate of the hydrophilizing agent after immersion in ethanol was 6%, indicating that the hydrophilizing agent was remained on the surface to maintain hydrophilicity of the membrane. The results are shown in Table 1.

The SEM photograph of the membrane cross-section is shown in FIG. 1.

Example 2

A flat membrane was prepared according to the Membrane Preparation Example 1 by using PPE and Pluronic F68 (a PPG-PEG block copolymer, number average molecular weight: 8,400, ADEKA Corp.) as a hydrophilizing agent.

The membrane thickness was 180 μm, porosity was 80%, water permeability was $37.7 \times 10^{-7}$ (m$^3$/(hr·m$^2$·Pa)), and the maximum pore diameter was 154 nm. The contact angle with water was 64°, and the surface coating rate of hydrophilizing agent of the membrane was 39%. The surface coating rate of the hydrophilizing agent after immersion in ethanol was 13%, indicating that the hydrophilizing agent was remained on the surface to maintain hydrophilicity of the membrane. The color difference degree of ΔE* before and after γ-ray irradiation was 3.62 at 25 KGy and 4.01 at 57 KGy. The results are shown in Table 1.

Figure 2:
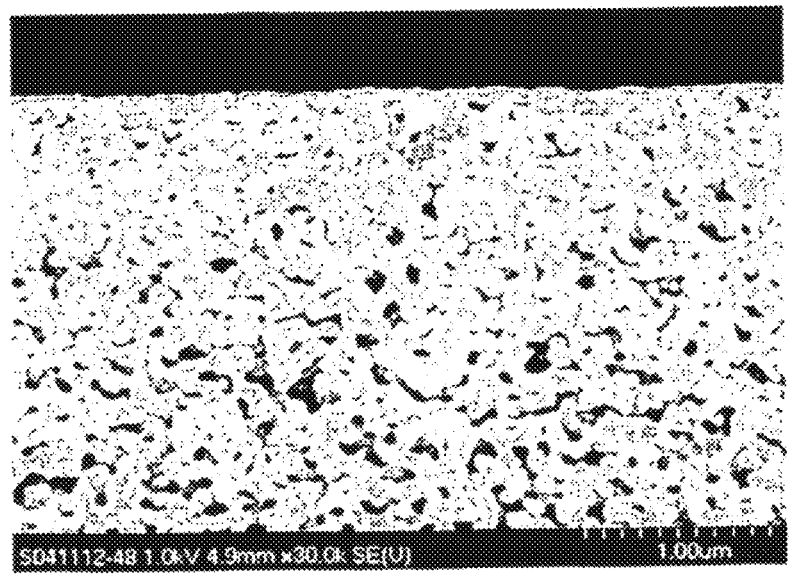
FIG. 2 is an SEM photograph of Example 2.

The SEM photograph of the membrane cross-section is shown in FIG. 2.

Example 3

A polystyrene-polyethylene glycol block copolymer was prepared according to the Preparation Example of polystyrene-polyethylene glycol block copolymer. The composition ratio of polystyrene and polyethylene glycol was 62/38 (wt %), the number average molecular weight was 20,100, and the molecular weight distribution was 1.7. A flat membrane was prepared from PPE and the polystyrene-polyethylene glycol block copolymer according to Membrane Preparation Example 1.

The membrane thickness was 188 μm, the maximum pore diameter was 82 nm, and the contact angle with water was 67. The surface coating rate of hydrophilizing agent of the membrane was 28%. The surface coating rate of the hydrophilizing agent after immersion in ethanol was 28%, indicating that the hydrophilizing agent was remained on the surface to maintain hydrophilicity of the membrane. The results are shown in Table 1.

Example 4

Hollow fiber membrane was prepared from PPE and Pluronic F68 (a polypropylene glycol-PEG block copolymer, number average molecular weight: 8,400, ADEKA Corp.) according to Membrane Preparation Example 2 by using NMP/water (70/30% by weight) as an internal coagulating liquid, at a wind-up speed of 4,200 m/hour.

The membrane thickness was 28 μm, the internal diameter was 169 μm, and the maximum pore diameter was 142 nm. The surface coating rate of hydrophilizing agent of the membrane was 40%. The surface coating rate of the hydrophilizing agent after immersion in ethanol was 12%, indicating that the hydrophilizing agent was remained on the surface to maintain hydrophilicity of the membrane. The permeation rate of IgG monomer was 20% and the permeation rate of IgG dimer was 11%, indicating that the permeation rate differs according to the size, and thus the membrane exhibits separation performance. The results are shown in Table 1.

Example 5

Hollow fiber membrane was prepared from PPE and Pluronic F68 (a PPG-PEG block copolymer, number average molecular weight: 8,400, ADEKA Corp.) according to Membrane Preparation Example 2 by using ethylene glycol (Wako Pure Chemical Industries, Ltd., hereinafter abbreviate to "EG") as an internal coagulating liquid, at a wind-up speed of 4,200 m/hour.

The membrane thickness was 30 μm, the internal diameter was 184 μm, and the maximum pore diameter was 119 nm. The surface coating rate of hydrophilizing agent of the membrane was 37%. The surface coating rate of the hydrophilizing agent after immersion in ethanol was 12%, indicating that the hydrophilizing agent was remained on the surface to maintain hydrophilicity of the membrane. The permeation rate of IgG monomer was 14% and the permeation rate of IgG dimer was 5%, indicating that the permeation rate differs according to the size, and thus the membrane exhibits separation performance. The results are shown in Table 1.

Example 6

Hollow fiber membrane was prepared from PPE and polystyrene-polyethylene glycol block copolymer, prepared in Example 3, according to Membrane Preparation Example 2 by using NMP/water (70/30 wt %) as an internal coagulating liquid, at a wind-up speed of 4,200 m/hour.

The membrane thickness was 30 μm, the internal diameter was 173 μm, and the maximum pore diameter was 90 nm. The surface coating rate of hydrophilizing agent of the membrane was 38%. The surface coating rate of the hydrophilizing agent after immersion in ethanol was 36%, indicating that the hydrophilizing agent was remained on the surface to maintain hydrophilicity of the membrane. The amount of protein adsorption was 2.5 μg/cm$^2$, indicating reduction as compared with a membrane made only from PPE. The permeation rate of IgG monomer was 8% and the permeation rate of IgG dimer was 3%, indicating that the permeation rate differs according to the size, and thus the membrane exhibits separation performance. The results are shown in Table 1.

Figure 3:
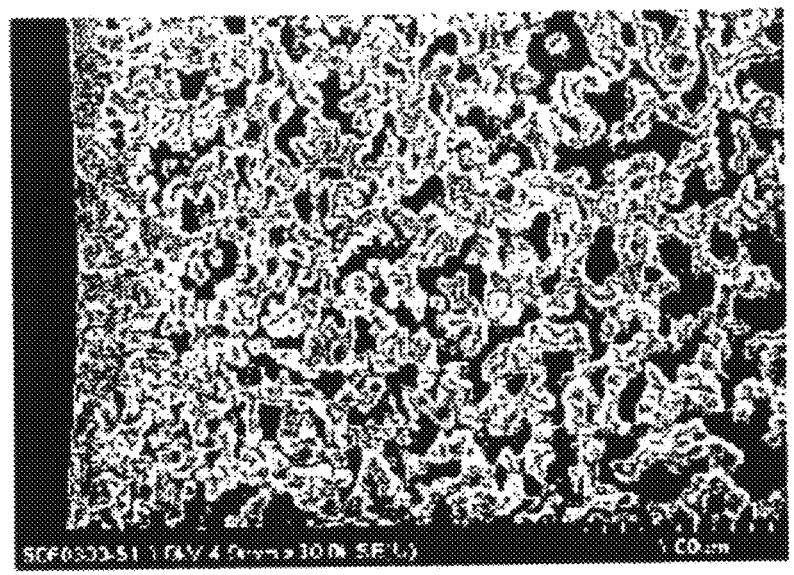
FIG. 3 is an SEM photograph of Example 6.

The SEM photograph of the membrane cross-section is shown in FIG. 3.

Example 7

A polystyrene-polyethylene glycol block copolymer was prepared according to the Preparation Example of polystyrene-polyethylene glycol block copolymer. The composition ratio of polystyrene and polyethylene glycol was 75/25 (wt %), the number average molecular weight was 24,300, and the molecular weight distribution was 1.8. A hollow fiber membrane was prepared from PPE and a polystyrene-polyethylene glycol block copolymer according to Membrane Preparation Example 2 by using EG as an internal coagulating liquid, at a wind-up speed of 4,200 m/hour.

The membrane thickness was 28 μm, and the internal diameter was 185 μm, and the maximum pore diameter was 85 nm. The surface coating rate of hydrophilizing agent of the membrane was 38%. The surface coating rate of the hydrophilizing agent after immersion in ethanol was 36%, indicating that the hydrophilizing agent was remained on the surface to maintain hydrophilicity of the membrane. The results are shown in Table 1.

Example 8

A hollow fiber membrane was prepared from PPE and a polystyrene-polyethylene glycol block copolymer, prepared in Example 3, according to Membrane Preparation Example 2 by using a casting/spinning solution consisting of 252 g of PPE, 99 g of the polystyrene-polyethylene glycol block copolymer and 1.449 g of NMP, NMP/water (70/30% by weight) as an internal coagulating liquid, at a wind-up speed of 4,200 m/hour.

The membrane thickness was 26 μm, internal diameter was 172 μm, water permeability was $59.0 \times 10^{-7}$ (m$^3$/(hr·m$^2$·Pa)), and the maximum pore diameter was 105 nm. The amount of protein adsorption was 0.3 μg/cm$^2$, which was an extremely small amount. The permeation rate of IgG monomer was 18% and the permeation rate of IgG dimer was 7%, indicating that the permeation rate differs according to the size, and thus the membrane exhibits separation performance. The results are shown in Table 1.

Example 9

A hollow fiber membrane was prepared from PPE and Pluronic F68 (a PPG-PEG block copolymer, number average molecular weight: 8,400, ADEKA Corp.) as a hydrophilizing agent according to Membrane Preparation Example 2 by using NMP/water (50/50 wt %) as an internal coagulating liquid, at a wind-up speed of 4,200 m/hour.

The membrane thickness was 35 μm, internal diameter was 197 μm, porosity was 74%, and water permeability was $2.5 \times 10^{-7}$ (m$^3$/(hr·m$^2$·Pa)). The membrane strength before γ-ray irradiation was 7.0N, whereas the strength after irradiating at a dose of 25 KGy was 7.1N and at a dose of 57 KGy was 7.0N, indicating that there was no deterioration in the strength before and after irradiation. In respect of ductility, the membrane showed ductility before irradiation of 147%, and after irradiation of 147% (at 25 KGy) and 143% (at 57 KGy), indicating that there was no change before and after irradiation and thus no deterioration of ductility. The results are shown in Table 1.

Figure 4:
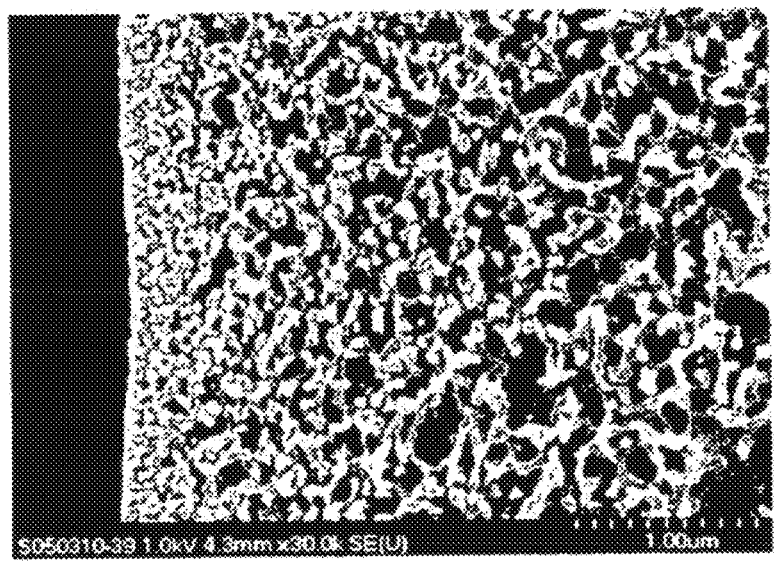
FIG. 4 is an SEM photograph of Example 9.

The SEM photograph of the membrane cross-section is shown in FIG. 4.

Example 10

A hollow fiber membrane was prepared from PPE and Pluronic F68 (a polypropylene glycol-PEG block copolymer, number average molecular weight: 8,400, ADEKA Corp.) as a hydrophilizing agent according to Membrane Preparation Example 2 by using EG as an internal coagulating liquid, at a wind-up speed of 4,200 m/hour.

Example 11

A hollow fiber membrane was prepared from PPE and Pluronic F68 (a polypropylene glycol-PEG block copolymer, number average molecular weight: 8,400, ADEKA Corp.) as a hydrophilizing agent according to Membrane Preparation Example 2 by using EG/NMP (50/50 wt %) as an internal coagulating liquid, at a wind-up speed of 4,200 m/hour.

The membrane thickness was 27 μm, internal diameter was 170 μm, porosity was 73%, and water permeability was 51.5×$10^{-7}$ (m$^3$/(hr·m$^2$·Pa)). The results are shown in Table 1.

Example 12

A hollow fiber membrane was prepared from PPE and Pluronic F68 (a polypropylene glycol-PEG block copolymer, number average molecular weight: 8,400, ADEKA Corp.) as a hydrophilizing agent according to Membrane Preparation Example 2 by using tetraethylene glycol (Wako Pure Chemical Industries, Ltd., hereinafter abbreviate to "TEG") as an internal coagulating liquid, at a wind-up speed of 4,200 m/hour.

The membrane thickness was 21 μm, internal diameter was 203 μm, and porosity was 69%. The membrane had a structure with no macrovoids on the cross-section of the membrane. The water permeability was 30.3×$10^{-7}$ (m$^3$/(hr·m$^2$·Pa)). The results are shown in Table 1.

Example 13

A hollow fiber membrane was prepared from PPE and Pluronic F68 (a polypropylene glycol-PEG block copolymer, number average molecular weight: 8,400, ADEKA Corp.) as a hydrophilizing agent according to Membrane Preparation Example 2 by using 1,4-butane diol (Wako Pure Chemical Industries, Ltd., hereinafter abbreviate to "BD") as an internal coagulating liquid, at a wind-up speed of 4,200 m/hour.

The membrane thickness was 25 μm, internal diameter was 190 μm, and porosity was 73%. The membrane had a structure with no macrovoids on the cross-section. The water permeability was 83.1×$10^{-7}$ (m$^3$/(hr·m$^2$·Pa)). The results are shown in Table 1.

Comparative Example 1

A flat membrane was prepared using only PPE in the same manner as Membrane Preparation Example 1, except that a hydrophilizing agent was not added and a casting/spinning solution consisting of 2 g of PPE and 8 g of NMP was used.

The membrane thickness was 148 μm, porosity was 71%, water permeability was 5.8×$10^{-7}$ (m$^3$/(hr·m$^2$·Pa)), the maximum pore diameter was 69 nm, and the contact angle with water was 97°. The results are shown in Table 1.

The color difference degree of ΔE* before and after γ-ray irradiation was 2.48 at 25 KGy and 3.07 at 57 KGy. The membrane strength before γ-ray irradiation was 8.2N, whereas the strength after irradiating at a dose of 25 KGy was 8.0N, at a dose of 57 KGy was 8.2N, indicating that there was no deterioration in the strength. In respect of ductility, the membrane showed ductility before irradiation of 127%, and after irradiation of 126% (at 25 KGy) and 130% (at 57 KGy), indicating that there was no deterioration of ductility. The membrane showed a high protein adsorption of 3.8 μg/cm$^2$.

The both permeabilities of IgG monomer and dimer were not more than 1%. It is assumed that the pores were blocked by protein adsorption. The results are shown in Table 1.

Figure 5:
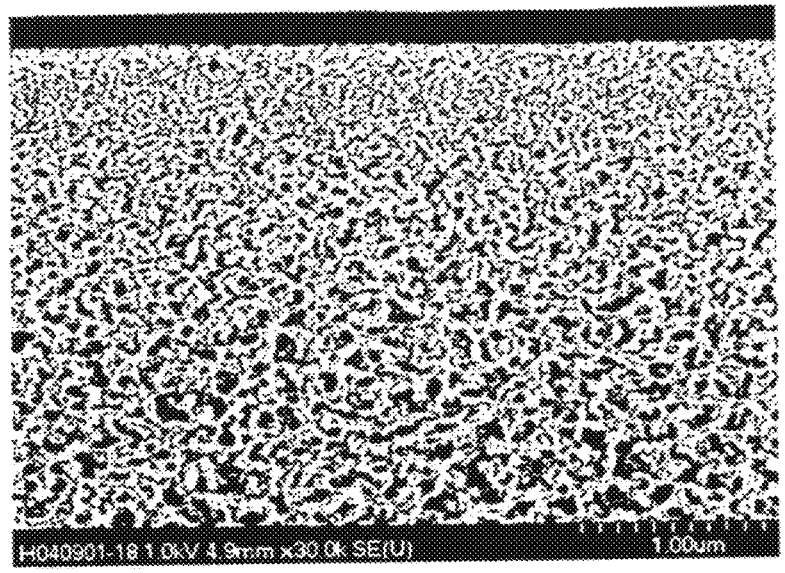
FIG. 5 is an SEM photograph of Comparative Example 1.

The SEM photograph of the membrane cross-section is shown in FIG. 5.

Comparative Example 2

The PPE unsymmetrical gas separation membrane disclosed in JP-A-H03-6527 was prepared. 2.0 g of PPE was added to 8.0 g of NMP and heated to 110° C. to dissolve PPE, thereby obtaining a polymer solution. The polymer solution was gently dropped onto a glass plate heated at 110° C., uniformly spread using an applicator, dried as-is for three minutes, and immersed in a coagulating liquid (purified water) at 25° C. to obtain a polymer membrane with a light-white color. The flat membrane was immersed in and washed with water at 25° C. with repeating several times, and allowed to stand to dry.

The resulting membrane had a thickness of 99 μm and porosity of 51%, and could not pass water therethrough during the water permeability test. Therefore, the water permeability was zero (m$^3$/(hr·m$^2$·Pa)). The test for measuring the maximum pore diameter was omitted because gas did not permeate through the membrane under 1.5 MPa, which was the pressure limit of the instrument. The results are shown in Table 1.

The PPE asymmetrical gas separation membrane prepared according to the disclosure in JP-A-H03-6527 did not show any water permeability. This is considered to be because the membrane surface is non-porous. The cross-sectional inspection result by SEM (FIG. 6) also shows that, differing from the membranes of Examples, the membrane of the Comparative Example 2 has almost no voids on the surface.

Figure 6:
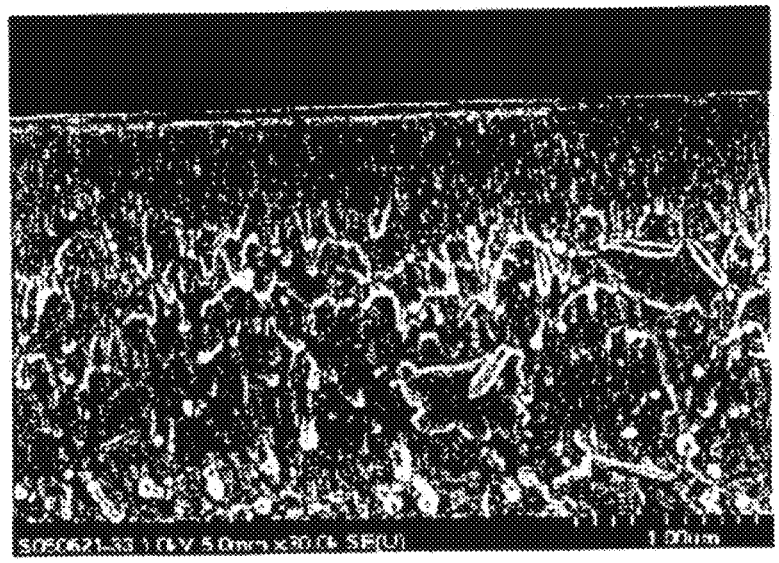
FIG. 6 is an SEM photograph of Comparative Example 2.

The SEM photograph of the membrane cross-section is shown in FIG. 6.

Comparative Example 3

A flat membrane was obtained in the same manner as in Preparation Example 1, except for using PSf ("P-1700", Solvay Advanced Polymers, K. K.) instead of PPE and polyvinylpyrrolidone ("K-90" ISP Japan, Inc., hereinafter abbreviated to "PVP") as a hydrophilizing agent, and decreasing the temperature during membrane-forming, and the temperatures of the casting/spinning solution and the internal coagulating liquid to 60° C.

The membrane thickness was 159 μm, porosity was 84%, water permeability was 34.6×$10^{-7}$ (m$^3$/(hr·m$^2$·Pa)), average pore diameter was 72 nm, and the maximum pore diameter was 78 nm.

The color difference degree of ΔE* before and after γ-ray irradiation was 7.57 at 25 KGy and 11.16 at 57 KGy, showing a greater discoloration than in Example 2.

The membrane strength before γ-ray irradiation was 9.2N, whereas the strength after irradiating at a dose of 25 KGy was 8.0N and at a dose of 57 KGy was 8.2N, indicating that there was a decrease in the strength after irradiation. In respect of ductility, the membrane showed ductility before irradiation of 137%, and after irradiation of 117% (at 25 KGy) and 120% (at 57 KGy), indicating that the ductility deteriorated after irradiation. The results are shown in Table 1.

Figure 7:
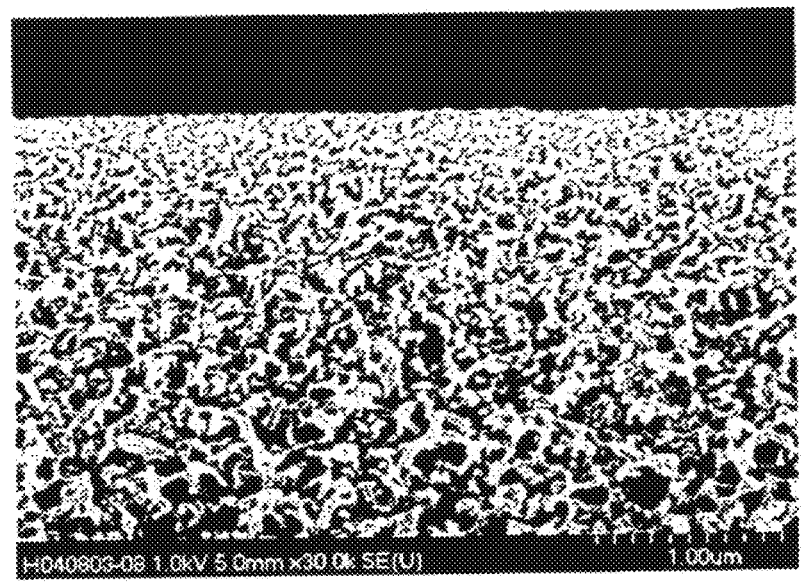
FIG. 7 is an SEM photograph of Comparative Example 3.

The SEM photograph of the membrane cross-section is shown in FIG. 7.

Comparative Example 4

A hollow fiber membrane was prepared in the same manner as in Preparation Example 2, except for using PSf instead of PPE and PVP as a hydrophilizing agent, decreasing the temperatures of membrane-forming, the casting/spinning solution and the internal coagulating liquid to 60° C., and the membrane wind-up speed of 3,000 m/hour.

The membrane thickness was 45 μm, internal diameter was 185 μm, porosity was 87%, and water permeability was $12.8 \times 10^{-7}$ (m$^3$/(hr·m$^2$·Pa)).

The color difference before and after γ-ray irradiation was not measured. The membrane strength before γ-ray irradiation was 6.6N, whereas the strength after irradiating at a dose of 25 KGy was 6.3N and at a dose of 57 KGy was 6.2N, indicating that there was a decrease in the strength. In respect of ductility, the membrane showed ductility before irradiation of 170%, and after irradiation of 150% (at 25 KGy) and 138% (at 57 KGy), indicating that the ductility deteriorated after irradiation. The results are shown in Table 1.

Figure 8:
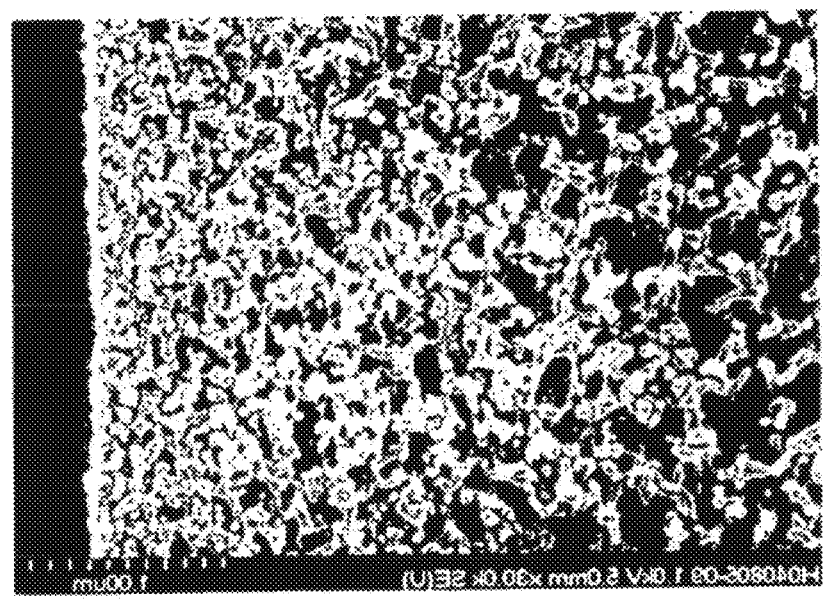
FIG. 8 is an SEM photograph of Comparative Example 4.

The SEM photograph of the membrane cross-section is shown in FIG. 8.

From the results of Examples 1 to 13, it can be seen that membranes having water permeability in a wide range can be prepared in various forms, including flat membranes and hollow fiber membranes. Based on the SEM photographs of the membranes cross-section showing the surface of the membrane of each Example comprising of agglomeration of minute agglomerated particles, it is considered that the pore diameter is controlled by controlling the size of the agglomerated particles and the agglomerating conditions.

Example 14

A module for treating liquid of the present invention was prepared using the hollow fiber membrane obtained in the Example 9.

First, the following casing parts were prepared. Two holes with a diameter of 14 mm were opened in a polycarbonate pipe (inner diameter: 34 mm, outer diameter: 37 mm, length: 0.36 m) in a manner so that the center of each hole was located at a point 45 mm from each end of the polycarbonate pipe. Then, polycarbonate pipes (inner diameter: 10 mm, outer diameter: 14 mm, length: 30 mm) applying an epoxy adhesive (a bond quick set 5-minute type, manufactured by Konishi, Inc., main material: 2.0 g, curing agent: 2.0 g) were inserted into each hole and attached thereto. The adhesive was then cured for 24 hours to obtain a main body of the casing. A polycarbonate pipe (inner diameter: 10 mm, outer diameter: 14 mm, length: 30 mm) was adhered to a disk (diameter: 40 mm, thickness: 2 mm), and the disk was adhered to another polycarbonate pipe (inner diameter: 37 mm, outer diameter: 40 mm, length: 20 mm). A pair of the object thus made of the polycarbonate pipes and the disk was prepared for use as covers to be connected to each end of the casing main body.

9,900 hollow fiber membranes obtained in Example 9 were bundled, lapped with a polyethylene film, and cut to a length of 0.40 m. An epoxy sealing agent (a bond quick set 5-minute type, manufactured by Konishi, Inc., main material: 100 g, curing agent: 100 g, acetone for viscosity adjustment: 30 g) was applied to one end surface of the cut bundle of hollow fiber membranes and cured for two hours to seal the end.

The hollow fiber membrane bundle was inserted into the casing main body from the unsealed end, while removing the polyethylene film. Thereafter, the unsealed end of the hollow fiber membrane bundle protruding from the casing main body was cut along the end of the casing main body to obtain a flat and smooth end surface.

A tube for injecting a sealing material was attached to the flat and smooth end surface and the main body of the casing was secured on a rotating table, with coinciding the centers of gravity of the table and the casing main body. The sealing agent was injected while rotating the table at a rate of 1,000 rpm. The temperature of the sealing agent when injected was 40° C. During injecting, excess sealing agent was flowed out from a branch tube (inner diameter: 10 mm, outer diameter: 14 mm) attached to the casing main body. After rotation, the excess sealing agent was removed. After that, the sealing agent was cured for two hours.

Then, the first sealed side of the hollow fiber bundle protruding from the casing main body was cut along the end of the casing main body to obtain a flat and smooth end surface. Thereafter, the sealing agent was injected while rotating in the same manner, followed by curing for 24 hours.

The casing main body and the hollow fiber bundle filled therein were cut at points 40 mm from each end of the casing main body. A covers were caused to adhere to both ends of the casing main body with an adhesive, while the adhesive was carefully applied so that the adhesive was not attached to the cut end surface. The adhesive was cured for 24 hours.

Figure 9:
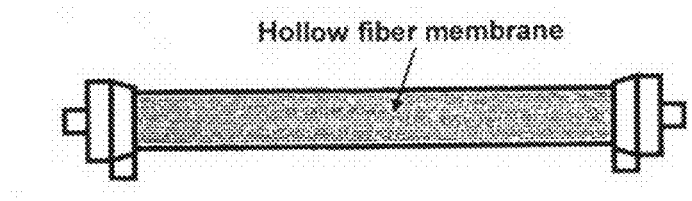
FIG. 9 is a module for treating liquid of Example 14.

In this manner, a module for treating liquid with a membrane area of 1.5 m$^2$ was prepared from 9,900 hollow fiber membranes, each having an internal diameter of 197 μm, a membrane thickness of 35 μm, and a length of 0.25 m. An outline of the module is shown in FIG. 9.

TABLE 1

Summary of experiment results

| | | Example 1 | Example 2 | Example 3 | Example 4 | Example 5 | Example 6 |
|---|---|---|---|---|---|---|---|
| | Form of membrane | Flat | Flat | Flat | Hollow fiber | Hollow fiber | Hollow fiber |
| Composition of casting/spinning solution | Membrane material | PPE | PPE | PPE | PPE | PPE | PPE |
| | Hydrophilizing agent | PEG | Pluronic F68 | PSt-PEG | Pluronic F68 | Pluronic F68 | PSt-PEG |
| | Good solvent | NMP | NMP | NMP | NMP | NMP | NMP |
| Weight ratio of components | Material/Hydrophilizing agent/good solvent | 16/4/80 | 16/4/80 | 16/4/80 | 16/4/80 | 16/4/80 | 16/4/80 |
| Coagulating liquid | Solvent | Water | Water | Water | NMP/Water | EG | NMP/Water |
| | Viscosity (20° C., cp) | 0.4 | 0.4 | 0.4 | — | 24 | — |
| Membrane Structure | Thickness d (μm)/inner diameter (μm) | 178/— | 180/— | 188/— | 28/169 | 30/184 | 30/173 |
| | Porosity α (%) | 78 | 80 | — | — | — | — |
| | Water permeability F (m$^3$ × (hr·m$^2$·Pa) × 10$^7$ | 35.0 | 37.7 | — | 47.8 | 37.0 | 54.6 |
| | Maximum pore diameter (nm) | 132 | 154 | 82 | 142 | 119 | 90 |

TABLE 1-continued

Summary of experiment results

|  |  |  |  |  |  |  |  |
|---|---|---|---|---|---|---|---|
|  | Macrovoid | No | No | — | — | — | — |
| Hydrophilicity | Contact degree with water (deg) | 87 | 64 | 67 | — | — | — |
| Surface coating rate (%) of hydrophilizing agent | Before immersing in ethanol | 14 | 39 | 28 | 40 | 37 | 39 |
|  | After immersing in ethanol | 6 | 13 | 28 | 12 | 12 | 38 |
| γ-ray irradiation test Color change | 25 KGy Δ E* | — | 3.62 | — | — | — | — |
|  | 57 KGy Δ E* | — | 4.01 | — | — | — | — |
| γ-ray irradiation test Strength | Before irradiation (N) | — | — | — | — | — | — |
|  | 25 KGy (N) | — | — | — | — | — | — |
|  | 57 KGy (N) | — | — | — | — | — | — |
| γ-ray irradiation test ductility | Before irradiation (%) | — | — | — | — | — | — |
|  | 25 KGy (%) | — | — | — | — | — | — |
|  | 57 KGy (%) | — | — | — | — | — | — |
| Protein adsorption (μg/cm²) |  | — | — | — | — | — | 2.5 |
| IgG monomer permeation rate (%) |  | — | — | — | 20 | 14 | 8 |
| IgG dimer permeation rate (%) |  | — | — | — | 11 | 5 | 3 |
| Ratio of IgG dimmer/IgG monomer permeation rate |  | — | — | — | 0.55 | 0.36 | 0.38 |

|  |  | Example 7 | Example 8 | Example 9 | Example 10 | Example 11 | Example 12 |
|---|---|---|---|---|---|---|---|
|  | Form of membrane | Hollow fiber | Hollow fiber | Hollow fiber | Hollow fiber | Hollow fiber | Hollow fiber |
| Composition of casting/spinning solution | Membrane material | PPE | PPE | PPE | PPE | PPE | PPE |
|  | Hydrophilizing agent | PSt-PEG | PSt-PEG | Pluronic F68 | Pluronic F68 | Pluronic F68 | Pluronic F68 |
|  | Good solvent | NMP | NMP | NMP | NMP | NMP | NMP |
| Weight ratio of components | Material/Hydrophilizing agent/good solvent | 16/4/80 | 28/11/161 | 32/11/160 | 32/11/157 | 32/11/157 | 32/11/157 |
| Coagulating liquid | Solvent | EG | NMP/Water | NMP/Water | EG | NMP/EG | TEG |
|  | Viscosity (20° C., cp) | 24 | — | 1.0 | 24 | 11 | 55 |
| Membrane Structure | Thickness d (μm)/inner diameter (μm) | 28/185 | 26/172 | 35/197 | 32/167 | 27/170 | 21/203 |
|  | Porosity α (%) | — | — | 74 | 78 | 73 | 69 |
|  | Water permeability F (m³ × (hr · m² · Pa) × 10⁷) | — | 59.0 | 2.5 | 39.7 | 51.5 | 30.3 |
|  | Maximum pore diameter (nm) | 85 | 105 | — | — | — | — |
|  | Macrovoid | — | — | Yes | Yes | No | No |
| Hydrophilicity | Contact degree with water (deg) | — | — | — | — | — | — |
| Surface coating rate (%) of hydrophilizing agent | Before immersing in ethanol | 38 | — | — | — | — | — |
|  | After immersing in ethanol | 36 | — | — | — | — | — |
| γ-ray irradiation test Color change | 25 KGy Δ E* | — | — | — | — | — | — |
|  | 57 KGy Δ E* | — | — | — | — | — | — |
| γ-ray irradiation test Strength | Before irradiation (N) | — | — | 7 | — | — | — |
|  | 25 KGy (N) | — | — | 7.1 | — | — | — |
|  | 57 KGy (N) | — | — | 7 | — | — | — |
| γ-ray irradiation test ductility | Before irradiation (%) | — | — | 147 | — | — | — |
|  | 25 KGy (%) | — | — | 147 | — | — | — |
|  | 57 KGy (%) | — | — | 173 | — | — | — |
| Protein adsorption (μg/cm²) |  | — | 0.3 | — | — | — | — |
| IgG monomer permeation rate (%) |  | — | 18 | — | — | — | — |
| IgG dimer permeation rate (%) |  | — | 7 | — | — | — | — |
| Ratio of IgG dimmer/IgG monomer permeation rate |  | — | 0.39 | — | — | — | — |

|  |  | Example 13 | Comparative Example 1 | Comparative Example 2 | Comparative Example 3 | Comparative Example 4 |
|---|---|---|---|---|---|---|
|  | Form of membrane | Hollow fiber | Flat | Flat | Flat | Hollow fiber |
| Composition of casting/spinning solution | Membrane material | PPE | PPE | PPE | PSf | PSf |
|  | Hydrophilizing agent | Pluronic F68 | None | None | PVP | PVP |
|  | Good solvent | NMP | NMP | NMP | NMP | NMP |
| Weight ratio of components | Material/Hydrophilizing agent/good solvent | 32/11/157 | 20/0/80 | 20/0/80 | 16/4/80 | 32/11/160 |
| Coagulating liquid | Solvent | BD | Water | Water | Water | NMP/Water |
|  | Viscosity (20° C., cp) | 89 | 0.4 | 0.4 | 0.4 | 1.0 |
| Membrane Structure | Thickness d (μm)/inner diameter (μm) | 25/190 | 148/— | 99/— | 159/— | 45/185 |
|  | Porosity α (%) | 73 | 71 | 51 | 84 | 87 |
|  | Water permeability F (m³ × (hr · m² · Pa) × 10⁷) | 83.1 | 5.8 | 0 | 34.6 | 12.8 |
|  | Maximum pore diameter (nm) | — | 69 | Unmeasurable | 78 | — |
|  | Macrovoid | No | No | — | — | — |
| Hydrophilicity | Contact degree with water (deg) | — | 97 | — | — | — |
| Surface coating rate (%) of hydrophilizing agent | Before immersing in ethanol | — | — | — | — | — |
|  | After immersing in ethanol | — | — | — | — | — |
| γ-ray irradiation test Color change | 25 KGy Δ E* | — | 2.48 | — | 7.57 | — |
|  | 57 KGy Δ E* | — | 3.07 | — | 11.2 | — |
| γ-ray irradiation test Strength | Before irradiation (N) | — | 8.2 | — | 9.2 | 6.6 |
|  | 25 KGy (N) | — | 8 | — | 8 | 6.3 |
|  | 57 KGy (N) | — | 8.2 | — | 8.2 | 6.2 |
| γ-ray irradiation test ductility | Before irradiation (%) | — | 127 | — | 137 | 170 |
|  | 25 KGy (%) | — | 126 | — | 117 | 150 |

TABLE 1-continued

| Summary of experiment results | | | | | |
|---|---|---|---|---|---|
| 57 KGy (%) | — | 130 | — | 120 | 138 |
| Protein adsorption (μg/cm²) | — | 3.8 | — | — | — |
| IgG monomer permeation rate (%) | — | <1 | — | — | — |
| IgG dimer permeation rate (%) | — | <1 | — | — | — |
| Ratio of IgG dimmer/IgG monomer permeation rate | — | — | — | — | — |

— indicates unmeasured

The invention claimed is:

1. A membrane for treating liquid made from an aromatic ether polymer shown by the following formula (1),

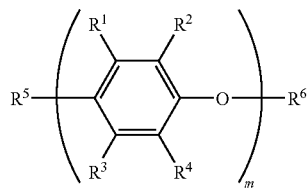

wherein $R^1$, $R^2$, $R^3$, $R^4$, $R^5$, and $R^6$ represent hydrogen, an organic functional group having 1 to 6 carbon atoms, or a non-protonic organic functional group having 6 or less carbon atoms containing oxygen, nitrogen, or silicon, and these groups may be same or differ from each other, and m is the number of repeating units, and the polymer may be a copolymer containing two or more different repeating units, wherein the aromatic ether polymer is hydrophilized with a hydrophilizing agent;

wherein the hydrophilizing agent is a block copolymer consisting of polystyrene and polyethylene glycol of the following formula:

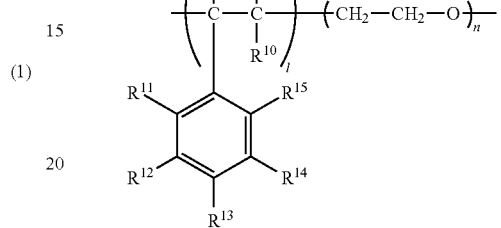

wherein $R^8$, $R^9$, $R^{10}$, $R^{11}$, $R^{12}$, $R^{13}$, $R^{14}$, and $R^{15}$ represent hydrogen, a halogen atom excluding fluorine, an organic functional group having 1 to 6 carbon atoms, or a functional group having 6 or less carbon atoms and containing oxygen, nitrogen, or silicon, and these groups may be the same or differ from each other; l is 2 or more; and n is 1 or more;

wherein said polyethylene glycol has a molecular weight of 2,000 to 50,000.

2. The membrane according to claim 1, wherein the aromatic ether polymer is not chemically modified by the hydrophilizing agent.

* * * * *